United States Patent
Kiriyama et al.

(10) Patent No.: US 11,592,746 B2
(45) Date of Patent: Feb. 28, 2023

(54) RADIATION-SENSITIVE RESIN COMPOSITION, RESIST PATTERN-FORMING METHOD, COMPOUND AND METHOD OF GENERATING ACID

(71) Applicant: JSR CORPORATION, Tokyo (JP)

(72) Inventors: Kazuya Kiriyama, Tokyo (JP); Katsuaki Nishikori, Tokyo (JP); Takuhiro Taniguchi, Tokyo (JP); Ken Maruyama, Tokyo (JP)

(73) Assignee: JSR CORPORATION, Tokyo (JP)

( * ) Notice: Subject to any disclaimer, the term of this patent is extended or adjusted under 35 U.S.C. 154(b) by 464 days.

(21) Appl. No.: 16/815,075

(22) Filed: Mar. 11, 2020

(65) Prior Publication Data

US 2020/0341376 A1 Oct. 29, 2020
US 2021/0263413 A9 Aug. 26, 2021

(30) Foreign Application Priority Data

Apr. 24, 2019 (JP) .............................. JP2019-083410

(51) Int. Cl.

| C07C 309/06 | (2006.01) |
|---|---|
| G03F 7/039 | (2006.01) |
| G03F 7/004 | (2006.01) |
| C08L 25/06 | (2006.01) |
| C08L 33/06 | (2006.01) |
| C07C 309/12 | (2006.01) |

(52) U.S. Cl.
CPC .......... *G03F 7/0392* (2013.01); *C07C 309/06* (2013.01); *C07C 309/12* (2013.01); *C08L 25/06* (2013.01); *C08L 33/064* (2013.01); *G03F 7/0045* (2013.01)

(58) Field of Classification Search
CPC ... C07C 381/12; C07C 309/06; C07C 312/12; C07C 309/12
See application file for complete search history.

(56) References Cited

U.S. PATENT DOCUMENTS

| 4,822,718 A | 4/1989 | Latham |
|---|---|---|
| 4,876,165 A | 10/1989 | Brewer |
| 4,910,122 A | 3/1990 | Arnold |
| 5,674,648 A | 10/1997 | Brewer |
| 11,163,232 B2 * | 11/2021 | Hatakeyama ......... C07C 303/32 |
| 2018/0267402 A1 * | 9/2018 | Hatakeyama ......... C08F 228/02 |
| 2018/0267403 A1 * | 9/2018 | Hatakeyama ......... G03F 7/0046 |
| 2018/0275512 A1 * | 9/2018 | Hatakeyama ....... C08F 220/283 |
| 2019/0155152 A1 * | 5/2019 | Aqad ........................ G03F 7/16 |
| 2021/0055652 A1 * | 2/2021 | Hatakeyama ........... G03F 7/168 |
| 2022/0146931 A1 * | 5/2022 | Shimada ............... C07C 309/12 |
| 2022/0171284 A1 * | 6/2022 | Lee ....................... G03F 7/0045 |

FOREIGN PATENT DOCUMENTS

| JP | S5993448 A | 5/1984 |
|---|---|---|
| JP | H0612452 B2 | 2/1994 |
| JP | H11212265 A | 8/1999 |
| JP | 2003005375 A | 1/2003 |
| JP | 2008083370 A | 4/2008 |
| JP | 2018005224 A | 1/2018 |
| JP | 2018159744 A | 10/2018 |
| JP | 2019061217 A | 4/2019 |

OTHER PUBLICATIONS

Office Action dated Oct. 25, 2022 in Japanese Patent Application No. 2019-083410 (with English translation).
Office Action dated Jan. 10, 2023 in Japanese Patent Application No. 2019-083410 (with English translation), 4 pages.

* cited by examiner

*Primary Examiner* — Amanda C. Walke
(74) *Attorney, Agent, or Firm* — Element IP, PLC

(57) ABSTRACT

A radiation-sensitive resin composition contains: a polymer that includes a structural unit including an acid-labile group; and a radiation-sensitive acid generating agent. The radiation-sensitive acid generating agent includes a sulfonate anion and a radiation-sensitive cation. The sulfonate anion includes two or more rings, and an iodine atom and a monovalent group having 0 to 10 carbon atoms which includes at least one of an oxygen atom and a nitrogen atom bond to at least one of the two or more rings. The ring is preferably an aromatic ring. The radiation-sensitive acid generating agent is preferably a compound represented by formula (1). In the formula (1), $A^1$ represents a group obtained from a compound which includes a ring having 3 to 20 ring atoms by removing (p+q+r+1) hydrogen atoms on the ring.

(1)

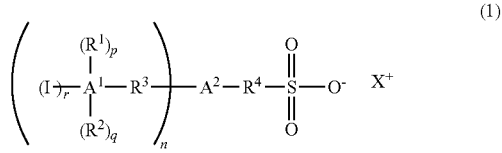

13 Claims, No Drawings

RADIATION-SENSITIVE RESIN COMPOSITION, RESIST PATTERN-FORMING METHOD, COMPOUND AND METHOD OF GENERATING ACID

CROSS-REFERENCE TO RELATED APPLICATIONS

The present application claims priority to Japanese patent application No. 2019-083410, filed Apr. 24, 2019, the contents of which are incorporated herein by reference in their entirety.

BACKGROUND OF THE INVENTION

Field of the Invention

The present invention relates to a radiation-sensitive resin composition, a resist pattern-forming method, a compound and a method of generating an acid.

Description of the Related Art

Microfabrication of various types of electronic device structures such as semiconductor devices and liquid crystal devices has been accompanied by a demand for further microfabrication of resist patterns in lithography processes, and a variety of radiation-sensitive resin compositions have been investigated for this purpose. Such a radiation-sensitive resin composition generates an acid in a light-exposed region upon irradiation with exposure light, e.g., a far ultraviolet ray such as an ArF excimer laser, an extreme ultraviolet ray (EUV), or an electron beam, to cause by a catalytic action of the acid a difference in a rate of dissolution in a developer solution between the light-exposed region and a light-unexposed region, thereby allowing a resist pattern to be formed on a substrate.

There has been a demand for such a radiation-sensitive resin composition not only to be superior in resolution and the like, but also to be superior in a depth of focus and an exposure latitude and to enable obtaining a resist pattern with a high process yield. To meet this demand, structures of polymers which may be contained in a radiation-sensitive resin composition have been extensively investigated (see Japanese Unexamined Patent Applications, Publication Nos. H11-212265, 2003-5375 and 2008-83370).

SUMMARY OF THE INVENTION

According to an aspect of the present invention, a radiation-sensitive resin composition includes a polymer that includes a structural unit including an acid-labile group, and a radiation-sensitive acid generating agent. The radiation-sensitive acid generating agent includes a sulfonate anion and a radiation-sensitive cation. The sulfonate anion includes two or more rings. An iodine atom and a monovalent group having 0 to 10 carbon atoms which includes at least one of an oxygen atom and a nitrogen atom are bonded to at least one of the two or more rings.

According to another aspect of the present specification, a resist pattern-forming method includes applying a radiation-sensitive resin composition directly or indirectly on a substrate to form a resist film. The resist film is exposed. The resist film exposed is developed. The radiation-sensitive resin composition includes a polymer that includes a structural unit including an acid-labile group, and a radiation-sensitive acid generating agent. The radiation-sensitive acid generating agent includes a sulfonate anion and a radiation-sensitive cation. The sulfonate anion includes two or more rings. An iodine atom and a monovalent group having 0 to 10 carbon atoms which includes at least one of an oxygen atom and a nitrogen atom are bonded to at least one of the two or more rings.

According to further aspect of the present specification, a compound is represented by formula (1):

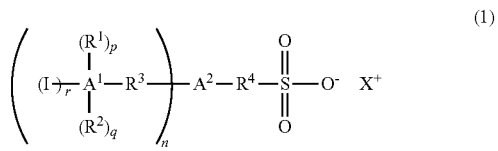

In the formula (1): $A^1$ represents a group obtained from a compound which comprises a ring having 3 to 20 ring atoms by removing (p+q+r+1) hydrogen atoms on the ring; Ie represents a monovalent group having 0 to 10 carbon atoms which comprises at least one of an oxygen atom and a nitrogen atom; $R^2$ represents a monovalent hydrocarbon group having 1 to 20 carbon atoms, a monovalent halogenated hydrocarbon group having 1 to 20 carbon atoms or a halogen atom; p is an integer of 1 to 10, q is an integer of 0 to 9 and r is an integer of 1 to 10, wherein (p+q+r) is no greater than 11; $R^3$ represents a single bond, —O— or —COO—; $A^2$ represents an organic group having a valency of (n+1) and having 3 to 30 carbon atoms that comprises a ring having 3 to 20 ring atoms; and n is an integer of 1 to 3. In a case in which there exist a plurality of $R^1$s, the plurality of $R^1$s are identical or different from each other, in a case in which there exist a plurality of $R^2$s, the plurality of $R^2$s are identical or different from each other, and in a case in which n is no less than 2, a plurality of $A^1$s are identical or different from each other, a plurality of $R^3$s are identical or different from each other, a plurality of p's are identical or different from each other, a plurality of q's are identical or different from each other, and a plurality of r's are identical or different from each other. $R^4$ represents a fluorinated alkanediyl group having 1 to 10 carbon atoms; and $X^+$ represents a monovalent radiation-sensitive onium cation.

According to further aspect of the present invention, a method of generating an acid includes irradiating the compound with a far ultraviolet ray, an extreme ultraviolet ray or an electron beam.

DESCRIPTION OF THE EMBODIMENTS

According to one embodiment of the invention made for solving the aforementioned problems, a radiation-sensitive resin composition contains: a polymer (hereinafter, may be also referred to as "(A) polymer" or "polymer (A)") having a structural unit that includes an acid-labile group; and a radiation-sensitive acid generating agent (hereinafter, may be also referred to as "(B) acid generating agent" or "acid generating agent (B)"), wherein the acid generating agent (B) includes a sulfonate anion and a radiation-sensitive cation, the sulfonate anion has two or more rings, and an iodine atom and a monovalent group having 0 to 10 carbon atoms which includes at least one of an oxygen atom and a nitrogen atom are bonded to at least one of the rings.

According to another embodiment of the invention made for solving the aforementioned problems, a resist pattern-forming method includes: applying a radiation-sensitive resin composition directly or indirectly on a substrate to form a resist film; exposing the resist film; and developing the resist film exposed, wherein the radiation-sensitive resin composition contains: the polymer (A) and the acid generating agent (B), wherein the acid generating agent (B) includes a sulfonate anion and a radiation-sensitive cation, wherein the sulfonate anion comprises two or more rings, and an iodine atom and a monovalent group having 0 to 10 carbon atoms which includes at least one of an oxygen atom and a nitrogen atom are bonded to at least one of the rings.

According to still another embodiment of the invention made for solving the aforementioned problems, a radiation-sensitive acid generating agent is represented by the following formula (1):

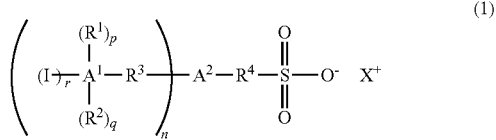

wherein, in the formula (1), $A^1$ represents a group obtained from a compound which comprises a ring having 3 to 20 ring atoms by removing (p+q+r+1) hydrogen atoms on the ring;

$R^1$ represents a monovalent group having 0 to 10 carbon atoms which comprises at least one of an oxygen atom and a nitrogen atom;

$R^2$ represents a monovalent hydrocarbon group having 1 to 20 carbon atoms, a monovalent halogenated hydrocarbon group having 1 to 20 carbon atoms or a halogen atom;

p is an integer of 1 to 10, q is an integer of 0 to 9 and r is an integer of 1 to 10, wherein (p+q+r) is no greater than 11;

$R^3$ represents a single bond, —O— or —COO—;

$A^2$ represents an organic group having a valency of (n+1) and having 3 to 30 carbon atoms that includes a ring having 3 to 20 ring atoms;

n is an integer of 1 to 3, wherein in a case in which there exist a plurality of $R^1$s, the plurality of $R^1$s are identical or different from each other, in a case in which there exist a plurality of $R^2$s, the plurality of $R^2$s are identical or different from each other, and in a case in which n is no less than 2, a plurality of A's are identical or different from each other, a plurality of $R^3$s are identical or different from each other, a plurality of "p"s are identical or different from each other, a plurality of "q"s are identical or different from each other, and a plurality of "r"s are identical or different from each other;

$R^4$ represents a fluorinated alkanediyl group having 1 to 10 carbon atoms; and $X^+$ represents a monovalent radiation-sensitive onium cation.

According to yet another embodiment of the invention made for solving the aforementioned problems, a compound is represented by the above formula (1).

According to the radiation-sensitive resin composition and the resist pattern-forming method of the embodiment of the present invention, even under current circumstances in which miniaturization of resist patterns has proceeded to a level for line widths of no greater than 40 nm, a resist pattern can be formed with a sensitivity, a depth of focus and an exposure latitude each being superior. The radiation-sensitive resin composition has a good sensitivity to EUV. The radiation-sensitive acid generating agent of the still another embodiment of the present invention can be suitably used as a radiation-sensitive acid generating component of the radiation-sensitive resin composition. The compound of the yet another embodiment of the present invention can be suitably used as a source material of the radiation-sensitive acid generating agent. Therefore, these can be suitably used for working processes of semiconductor devices, and the like, in which microfabrication is expected to be further in progress hereafter.

Radiation-Sensitive Resin Composition

The radiation-sensitive resin composition of one embodiment of the present invention contains the polymer (A) and the acid generating agent (B). The radiation-sensitive resin composition may also contain, as favorable components, an acid diffusion controller (hereinafter, may be also referred to as "(C) acid diffusion controller" or "acid diffusion controller (C)") and/or a polymer (hereinafter, may be also referred to as "(D) polymer" or "polymer (D)") having a percentage content by mass of fluorine atoms greater than that of the polymer (A), and usually contains a solvent (hereinafter, may be also referred to as "(E) solvent" or "solvent (E)"). The radiation-sensitive resin composition may also contain other optional component(s) within a range not leading to impairment of the effects of the present invention.

Due to containing the polymer (A) and the acid generating agent (B), the radiation-sensitive resin composition is superior in sensitivity, depth of focus and exposure latitude. Although not necessarily clarified and without wishing to be bound by any theory, the reason for achieving the effects described above by the radiation-sensitive resin composition due to having the constitution described above may be supposed as in the following, for example. In the acid generating agent (B), the sulfonate anion has two or more rings, and an iodine atom and a highly polar group that includes at least one of an oxygen atom and a nitrogen atom are bonded to at least one of the rings. By virtue of the iodine atom bonded to the ring to which the highly polar group is bonded, effective absorption of EUV is believed to be enabled, and as a result, the radiation-sensitive resin composition has improved sensitivity. In addition, by virtue of the sulfonate anion having two or more rings and the highly polar group, a diffusion length of an acid generated from the acid generating agent (B) that permits dissociation of the acid-labile group in the polymer (A) is appropriately shortened. As a result, the depth of focus and the exposure latitude of the radiation-sensitive resin composition are considered to be improved.

Each component will be described in the following.

(A) Polymer

The polymer (A) has a structural unit (hereinafter, may be also referred to as "structural unit (I)") that includes an acid-labile group. The "acid-labile group" as referred to herein means a group that substitutes for a hydrogen atom of a carboxy group, a hydroxy group or the like and that is dissociated by an action of an acid.

The polymer (A) preferably has in addition to the structural unit (I), a structural unit (hereinafter, may be also referred to as "structural unit (II)") that includes a lactone structure, a cyclic carbonate structure, a sultone structure or a combination thereof, and/or a structural unit (hereinafter, may be also referred to as "structural unit (III)") that includes a phenolic hydroxyl group, and may also have an other structural unit aside from the structural units (I) to (III). Each structural unit will be described in the following.

Structural Unit (I)

The structural unit (I) includes an acid-labile group.

Examples of the structural unit (I) include a structural unit (hereinafter, may be also referred to as "structural unit (I-1A), (I-1'A), (I-1B), (I-2A) or (I-2B)") represented by the following formula (2-1A), formula (2-1'A), formula (2-1B), formula (2-2A) or formula (2-2B), a structural unit (hereinafter, may be also referred to as "structural unit (I-3)") that includes an acetal structure, and the like.

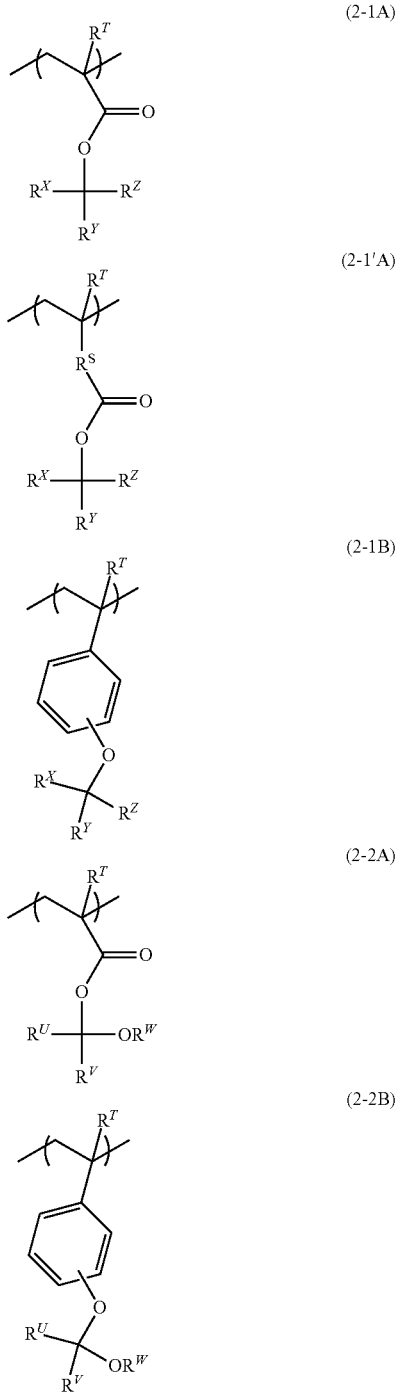

In the above formula (2-1A), $R^T$ represents a hydrogen atom, a fluorine atom, a methyl group or a trifluoromethyl group; $R^X$ represents a monovalent hydrocarbon group having 1 to 20 carbon atoms or a hydrogen atom; $R^Y$ and $R^Z$ each independently represent a monovalent hydrocarbon group having 1 to 20 carbon atoms, or $R^Y$ and $R^Z$ taken together represent a part of an alicyclic structure having 3 to 20 ring atoms constituted together with the carbon atom to which $R^Y$ and $R^Z$ bond.

In the above formula (2-1'A), $R^T$ represents a hydrogen atom, a fluorine atom, a methyl group or a trifluoromethyl group; $R^S$ represents a divalent organic group having 1 to 20 carbon atoms; $R^X$ represents a monovalent hydrocarbon group having 1 to 20 carbon atoms or a hydrogen atom; $R^Y$ and $R^Z$ each independently represent a monovalent hydrocarbon group having 1 to 20 carbon atoms, or $R^Y$ and $R^Z$ taken together represent a part of an alicyclic structure having 3 to 20 ring atoms constituted together with the carbon atom to which $R^Y$ and $R^Z$ bond.

In the above formula (2-1B), $R^T$ represents a hydrogen atom, a fluorine atom, a methyl group or a trifluoromethyl group; $R^X$ represents a monovalent hydrocarbon group having 1 to 20 carbon atoms; and $R^Y$ and $R^Z$ each independently represent a monovalent hydrocarbon group having 1 to 20 carbon atoms, or $R^Y$ and $R^Z$ taken together represent a part of an alicyclic structure having 3 to 20 ring atoms constituted together with the carbon atom to which $R^Y$ and $R^Z$ bond.

In the above formula (2-2A), $R^T$ represents a hydrogen atom, a fluorine atom, a methyl group or a trifluoromethyl group; $R^U$ represents a hydrogen atom or a monovalent hydrocarbon group having 1 to 20 carbon atoms; $R^V$ and $R^W$ each independently represent a monovalent hydrocarbon group having 1 to 20 carbon atoms, or $R^V$ and $R^W$ taken together represent a part of an aliphatic heterocyclic structure having 4 to 20 ring atoms constituted together with the carbon atom to which $R^U$ bonds and the oxygen atom adjacent to this carbon atom.

In the above formula (2-2B), $R^T$ represents a hydrogen atom, a fluorine atom, a methyl group or a trifluoromethyl group; $R^U$ represents a hydrogen atom or a monovalent hydrocarbon group having 1 to 20 carbon atoms; $R^V$ and $R^W$ each independently represent a monovalent hydrocarbon group having 1 to 20 carbon atoms, or $R^V$ and $R^W$ taken together represent a part of an aliphatic heterocyclic structure having 4 to 20 ring atoms constituted together with the carbon atom to which BY bonds and with the oxygen atom adjacent to this carbon atom.

In the structural units (I-1A) to (I-2B), $-CR^XR^YR^Z$ or $-R^UR^V(OR^W)$ bonding to an oxy-oxygen atom derived from the carboxy group or the phenolic hydroxyl group corresponds to the acid-labile group (a).

$R^T$ represents preferably a hydrogen atom or a methyl group in light of a degree of copolymerization of a monomer that gives a structural unit (I).

The "organic group" as referred to herein means a group that includes at least one carbon atom. Examples of the divalent organic group having 1 to 20 carbon atoms represented by $R^S$ include carbonyloxyhydrocarbon groups such as a carbonyloxybenzenediyl group, and the like.

The "hydrocarbon group" may involve a chain hydrocarbon group, an alicyclic hydrocarbon group and an aromatic hydrocarbon group. The "hydrocarbon group" may be a saturated hydrocarbon group or an unsaturated hydrocarbon group. The "chain hydrocarbon group" as referred to herein means a hydrocarbon group not having a ring structure but being constituted only from a chain structure, and involves both a linear hydrocarbon group and a branched hydrocarbon group. The "alicyclic hydrocarbon group" as referred to herein means a hydrocarbon group having as a ring structure not an aromatic ring structure but only an alicyclic structure, and involves both a monocyclic alicyclic hydrocarbon group and a polycyclic alicyclic hydrocarbon group. It is not necessary that the alicyclic hydrocarbon group is constituted from only the alicyclic structure, and a part thereof may also include a chain structure. The "aromatic hydrocarbon group" as referred to herein means a hydrocarbon group that includes an aromatic ring structure as the ring structure. It is not necessary that the aromatic hydrocarbon group is constituted from only the aromatic ring structure, and a part thereof may also include a chain structure and/or an alicyclic structure. The number of "ring atoms" as referred to herein means the number of atoms constituting the ring in an alicyclic structure, an aromatic ring structure, an aliphatic heterocyclic structure or an aromatic heterocyclic structure, and in the case of a polycyclic ring such as a fused ring or a bridged ring, the number of "ring atoms" means a sum total of the number of atoms constituting the polycyclic ring. For example, a naphthalene structure has 10 ring atoms, and an adamantane structure has 10 ring atoms.

The monovalent hydrocarbon group having 1 to 20 carbon atoms which may be represented by $R^X$, $R^Y$, $R^Z$, $R^U$, $R^V$ or $R^W$ is exemplified by a monovalent chain hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent chain hydrocarbon group having 1 to 20 carbon atoms include:

alkyl groups such as a methyl group, an ethyl group, a n-propyl group and an i-propyl group;

alkenyl groups such as an ethenyl group, a propenyl group and a butenyl group;

alkynyl groups such as an ethynyl group, a propynyl group and a butynyl group; and the like.

Examples of the monovalent alicyclic hydrocarbon group having 3 to 20 carbon atoms include:

monocyclic alicyclic saturated hydrocarbon groups such as a cyclopentyl group and a cyclohexyl group;

monocyclic alicyclic unsaturated hydrocarbon groups such as a cyclopentenyl group and a cyclohexenyl group;

polycyclic alicyclic saturated hydrocarbon groups such as a norbornyl group, an adamantyl group and a tricyclodecyl group;

polycyclic alicyclic unsaturated hydrocarbon groups such as a norbornenyl group and a tricyclodecenyl group; and the like.

Examples of the monovalent aromatic hydrocarbon group having 6 to 20 carbon atoms include:

aryl groups such as a phenyl group, a tolyl group, a xylyl group, a naphthyl group and an anthryl group;

aralkyl groups such as a benzyl group, a phenethyl group, a naphthylmethyl group and an anthrylmethyl group; and the like.

Examples of the alicyclic structure having 3 to 20 carbon atoms which may be constituted by $R^Y$ and $R^Z$ taken together together with the carbon atom include: monocyclic alicyclic structures such as a cyclopropane structure, a cyclobutane structure, a cyclopentane structure, a cyclohexane structure, a cyclopentene structure, and a cyclohexene structure; polycyclic alicyclic structures such as a norbornane structure and an adamantane structure; and the like.

Examples of the aliphatic heterocyclic structure having 4 to 20 carbon atoms which may be constituted by $R^V$ and $R^W$ taken together together with the carbon atom and oxygen atom include: monocyclic aliphatic heterocyclic structures such as an oxacyclobutane structure, an oxacyclopentane structure, an oxacyclohexane structure, an oxacyclopentene structure, and an oxacyclohexene structure; polycyclic aliphatic heterocyclic structures such as an oxanorbornane structure and an oxaadamantane structure; and the like.

Preferable examples of the structural unit (I-1A) include structural units (hereinafter, may be also referred to as "structural units (I-1A-1) to (I-1A-6)") represented by the following formulae (2-1A-1) to (2-1A-6), and preferable examples of the structural unit (I-1'A) include a structural unit (hereinafter, may be also referred to as "structural unit (I-1'A-1)") represented by the following formula (2-1'A-1).

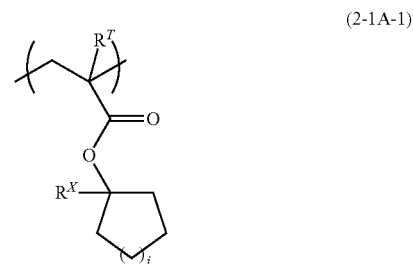

(2-1A-1)

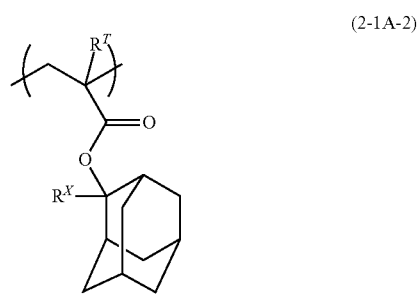

(2-1A-2)

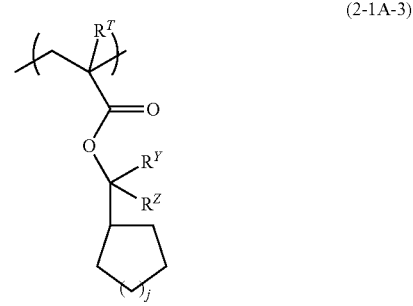

(2-1A-3)

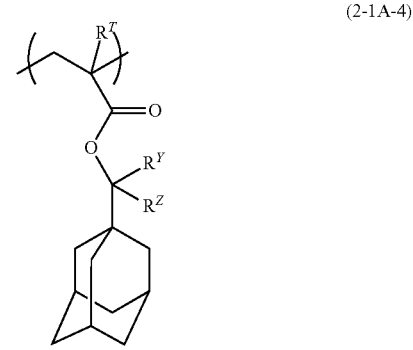

(2-1A-4)

-continued

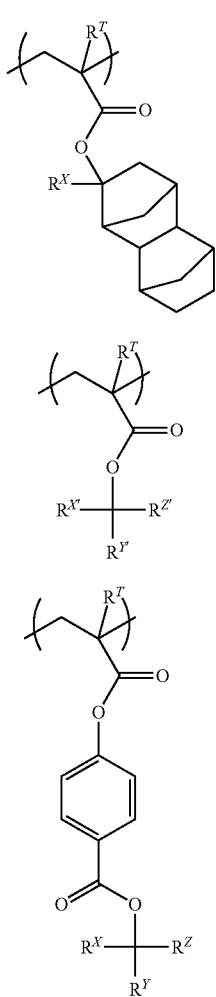

(2-1A-5)

(2-1A-6)

(2-1'A-1)

In the above formulae (2-1A-1) to (2-1A-5) and (2-1'A-1), $R^T$, $R^X$, $R^Y$ and $R^Z$ are as defined in the above formulae (2-1A) and (2-1'A), and i and j are each independently an integer of 1 to 4.

In the above formula (2-1A-6), $R^T$ represents a hydrogen atom, a fluorine atom, a methyl group or a trifluoromethyl group; $R^{X'}$, $R^{Y'}$ and $R^{Z'}$ each independently represent a monovalent chain hydrocarbon group having 1 to 20 carbon atoms.

Structural unit (I-3)

The structural unit (I-3) has an acetal structure. Examples of a group having the acetal structure include a group (hereinafter, may be also referred to as "group (Y)") represented by the following formula (3), and the like. The group (Y) generates *—OH, $R^JR^KC$=O and $R^LOH$ through degradation by an action of an acid. In the group (Y), —C($R^J$)($R^K$)(O$R^L$) corresponds to the acid-labile group.

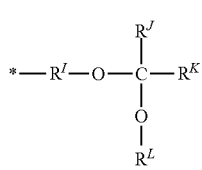

(3)

In the above formula (3), $R^I$ represents a single bond or a divalent hydrocarbon group having 1 to 20 carbon atoms; $R^J$ and $R^K$ each independently represent a hydrogen atom or a monovalent hydrocarbon group having 1 to 20 carbon atoms; $R^L$ represents a monovalent hydrocarbon group having 1 to 20 carbon atoms, or two or more of R', $R^J$, $R^K$ and $R^L$ taken together represent a part of a ring structure having 3 to 20 ring atoms constituted together with the carbon atom or the atom chain to which the two or more of $R^I$, $R^J$, $R^K$ and $R^L$ bond; and * denotes a binding site to a part other than the group (Y) in the structural unit (1-3).

Examples of the divalent hydrocarbon group having 1 to 20 carbon atoms represented by $R^I$ include groups obtained by removing one hydrogen atom from the monovalent hydrocarbon group having 1 to 20 carbon atoms exemplified as $R^X$, $R^Y$ and $R^Z$ in the above formulae (2-1A), (2-1'A) and (2-1B), and the like.

$R^I$ represents preferably a single bond or divalent chain hydrocarbon group having 1 to 20 carbon atoms, more preferably a divalent chain hydrocarbon group having 1 to 20 carbon atoms, still more preferably an alkanediyl group having 1 to 10 carbon atoms, and particularly preferably a methanediyl group.

Examples of the monovalent hydrocarbon group having 1 to 20 carbon atoms which may be represented by $R^J$, $R^K$ or $R^L$ include groups similar to groups exemplified as the monovalent hydrocarbon group having 1 to 20 carbon atoms which may be represented by $R^X$, $R^Y$ or $R^Z$ in the above formulae (2-1A), (2-1'A) and (2-1B), and the like.

$R^J$ and $R^K$ each represent preferably a hydrogen atom or a chain hydrocarbon group, more preferably a hydrogen atom or an alkyl group, and still more preferably a hydrogen atom or a methyl group. $R^Z$ represents preferably a chain hydrocarbon group, more preferably an alkyl group, and particularly preferably a methyl group.

$R^I$ represents preferably a single bond or a chain hydrocarbon group, more preferably a chain hydrocarbon group, still more preferably an alkanediyl group, and particularly preferably a methanediyl group.

Examples of the ring structure having 3 to 20 ring atoms which may be constituted from $R^J$ and $R^K$ include alicyclic structures such as a cyclopentane structure and a cyclohexane structure, and the like.

Examples of the ring structure having 4 to 20 ring atoms which may be constituted from $R^I$ and $R^J$ or $R^K$ and which may be constituted from $R^I$ or $R^K$ and $R^K$ include oxacycloalkane structures such as an oxacyclopentane structure and an oxacyclohexane structure, and the like.

Examples of the ring structure having 5 to 20 ring atoms which may be constituted from $R^I$ and $R^L$ include 1,3-dioxacycloalkane structures such as a 1,3-dioxacyclopentane structure, and the like.

The group (Y) is preferably a 1-(tetracyclododecan-2-yloxy)ethan-1-yloxy group.

The structural unit (I) is preferably the structural unit (I-1A) or (I-1'A), and more preferably the structural unit (I-1A-1) to (I-1A-3), (I-1A-5), (I-1A-6) or (I-1' A-1).

The lower limit of a proportion of the structural unit (I) contained with respect to total structural units constituting the polymer (A) is preferably 10 mol %, more preferably 20 mol %, still more preferably 30 mol %, and particularly preferably 40 mol %. The upper limit of the proportion of the structural unit (I) is preferably 90 mol %, more preferably 80 mol %, still more preferably 70 mol %, and particularly preferably 60 mol %. When the proportion of the structural unit (I) falls within the above range, the sensitivity, the depth of focus and the exposure latitude of the radiation-sensitive resin composition can be further improved.

Structural Unit (II)

The structural unit (II) includes a lactone structure, a cyclic carbonate structure, a sultone structure or a combination thereof. When the polymer (A) has the structural unit (II), solubility of the resist film into a developer solution can be more adequately adjusted, and as a result, the sensitivity, the depth of focus and the exposure latitude of the radiation-sensitive resin composition can be further improved.

Examples of the structural unit (II) include structural units represented by the following formulae, and the like.

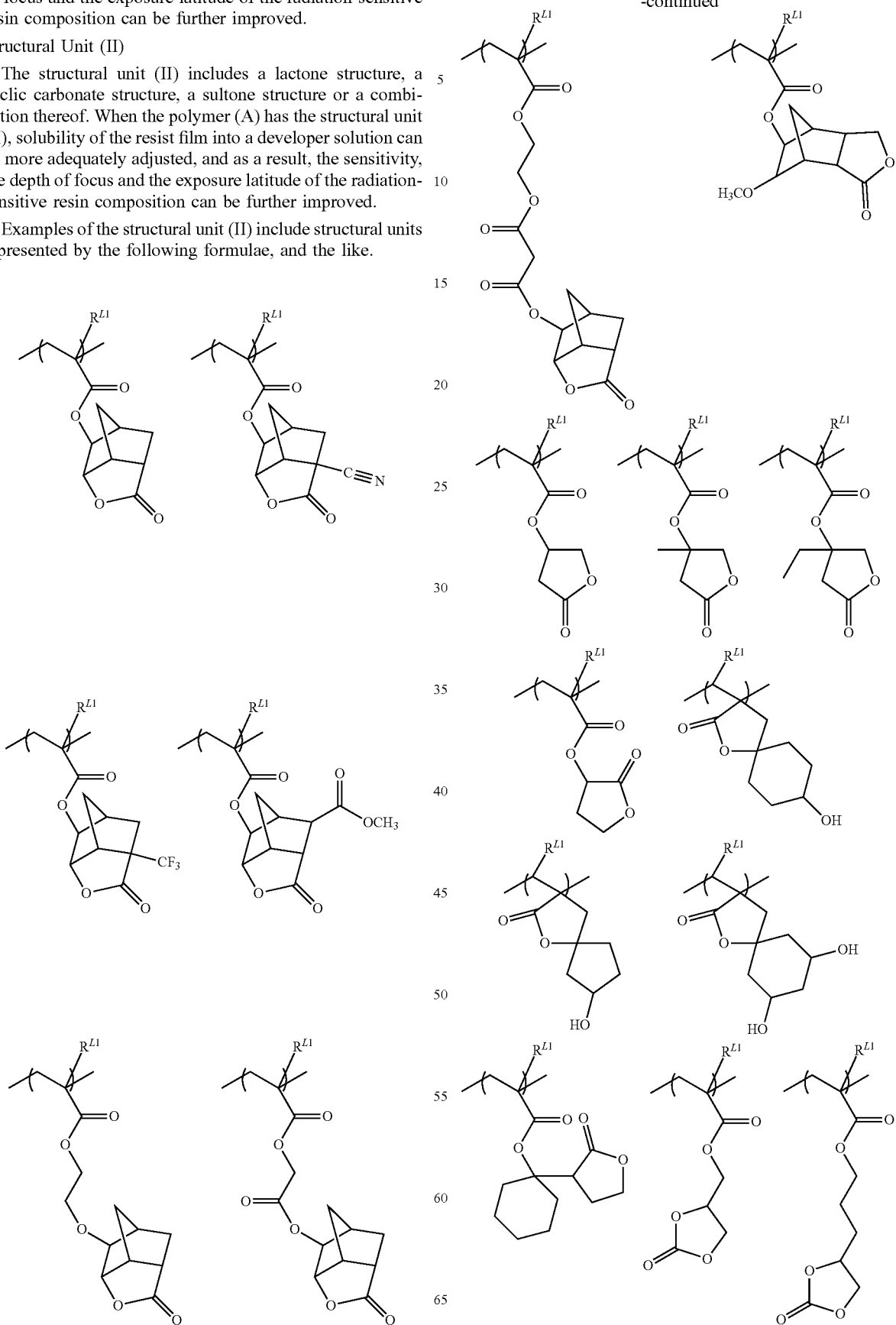

-continued
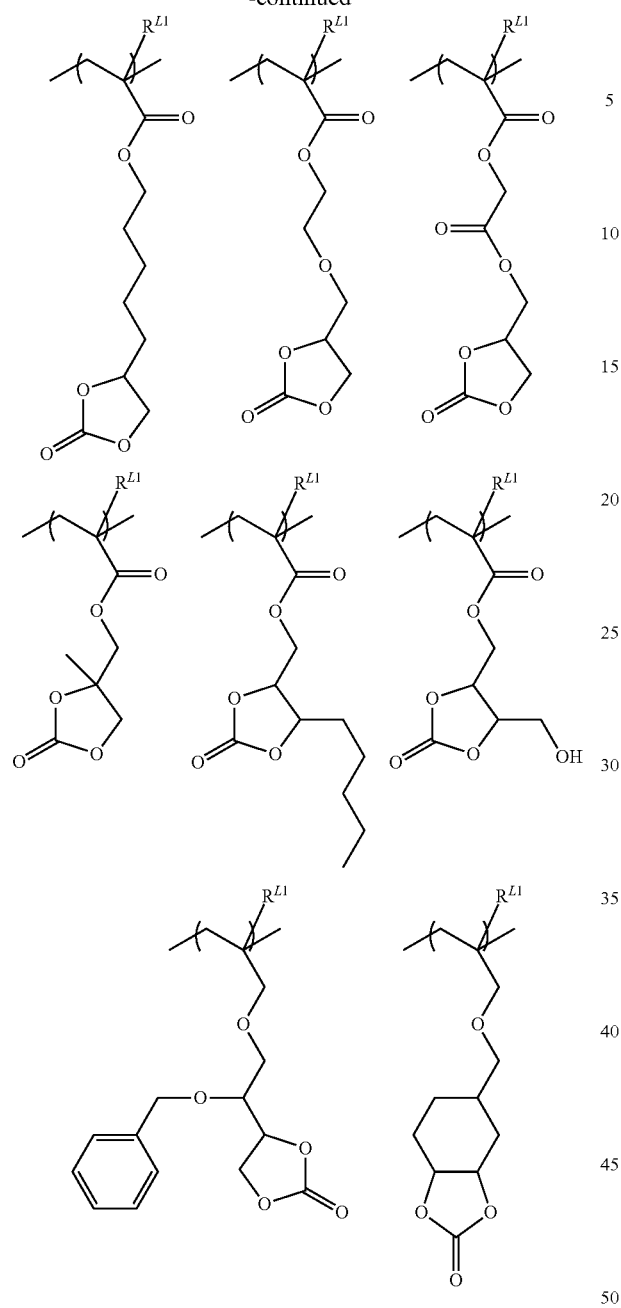
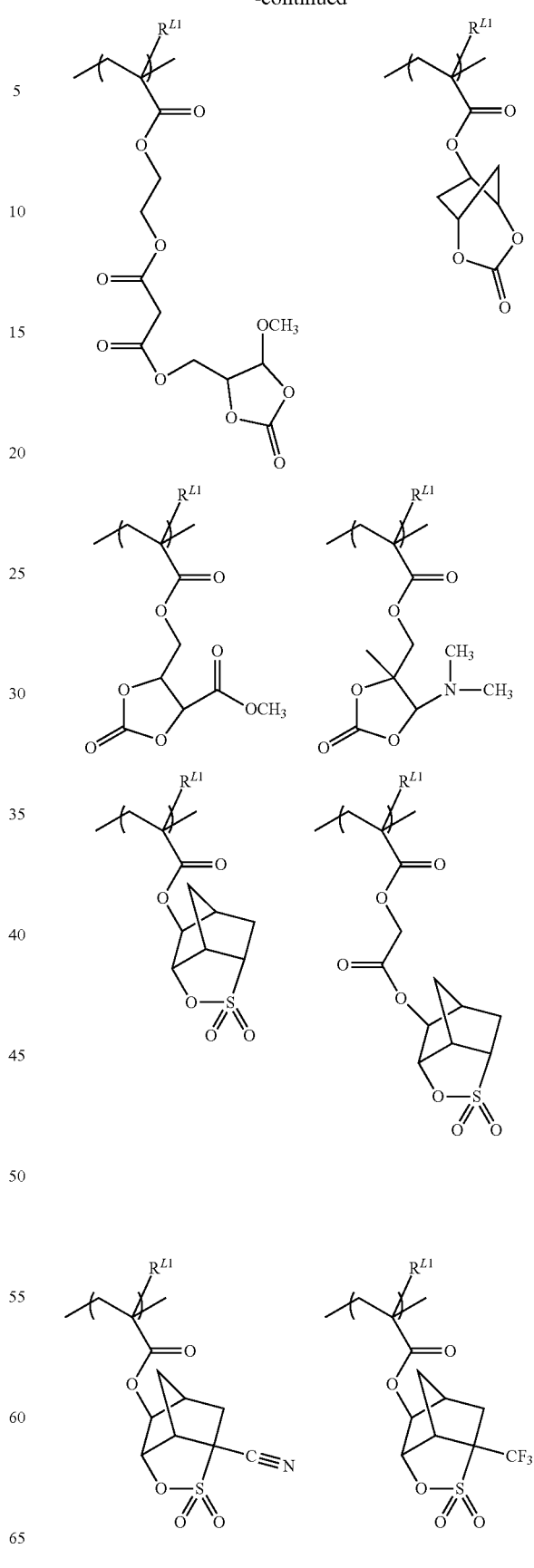

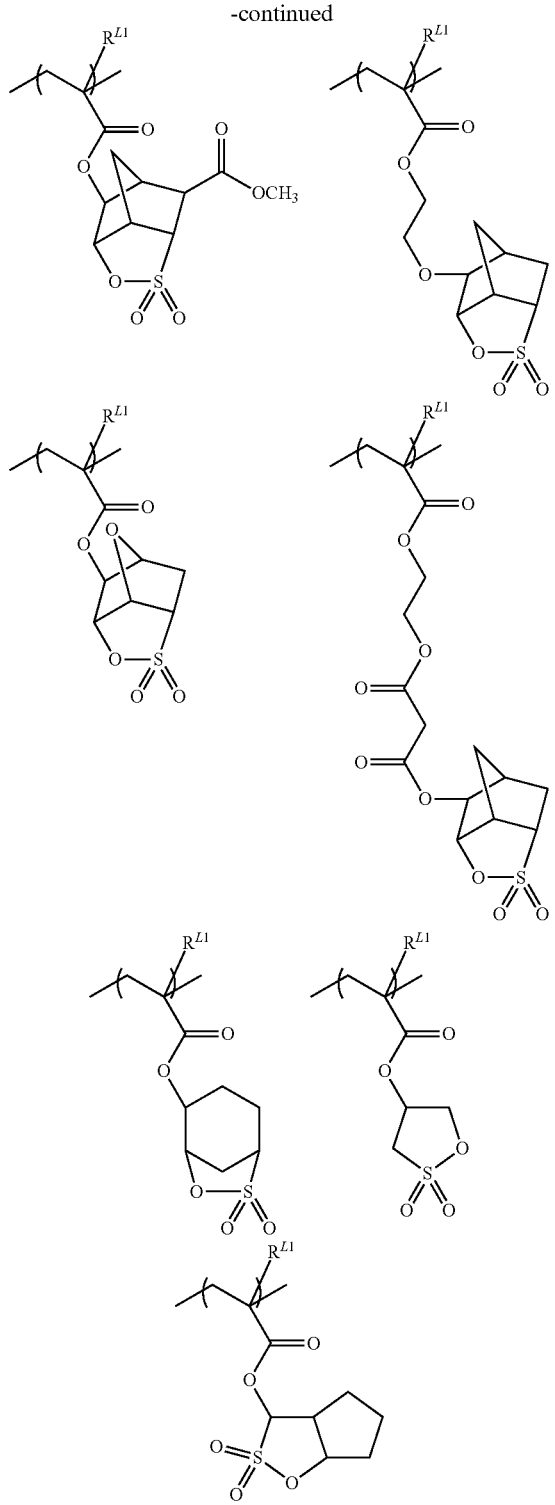

In the above formulae, $R^{L1}$ represents a hydrogen atom, a fluorine atom, a methyl group, or a trifluoromethyl group.

The structural unit (II) is preferably a structural unit that includes a norbornane-2,6-lactone structure, a structural unit that includes a γ-butyrolactone structure, a structural unit that includes an ethylene carbonate structure, or a structural unit that includes a norbornane-2,6-sultone structure.

In a case in which the polymer (A) has the structural unit (II), the lower limit of a proportion of the structural unit (II) contained with respect to the total structural units constituting the polymer (A) is preferably 10 mol %, more preferably 20 mol %, and still more preferably 30 mol %. The upper limit of the proportion of the structural unit (II) is preferably 70 mol %, more preferably 60 mol %, and still more preferably 50 mol %. When the proportion of the structural unit (II) falls within the above range, the sensitivity, the depth of focus and the exposure latitude of the radiation-sensitive resin composition can be further improved.

Structural Unit (III)

The structural unit (III) includes a phenolic hydroxyl group. The "phenolic hydroxyl group" as referred to herein is not limited to a hydroxy group directly bonding to a benzene ring, and means an entirety of hydroxy groups directly bonding to aromatic rings. When the polymer (A) has the structural unit (III), the solubility of the resist film into a developer solution can be more adequately adjusted, and as a result, the sensitivity, the depth of focus and the exposure latitude of the radiation-sensitive resin composition can be further improved. Furthermore, in a case of an exposure to KrF, an exposure to EUV or an exposure to an electron beam, the sensitivity of the radiation-sensitive resin composition can be further improved.

Examples of the structural unit (III) include a structural unit represented by the following formula (4), and the like.

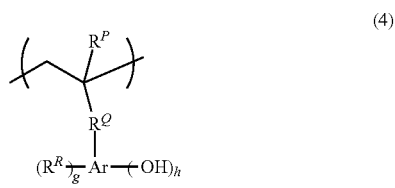

(4)

In the above formula (4), $R^1$ represents a hydrogen atom, a fluorine atom, a methyl group or a trifluoromethyl group; RQ represents a single bond, —O—, —COO— or —CONH—; Ar represents a group obtained by removing (g+h+1) hydrogen atoms on aromatic rings from an arene having 6 to 20 ring atoms; g is an integer of 0 to 10, wherein in a case in which g is 1, $R^R$ represents a monovalent organic group having 1 to 20 carbon atoms or a halogen atom, or in a case in which g is no less than 2, a plurality of $R^R$s are identical or different from each other and each represents a monovalent organic group having 1 to 20 carbon atoms or a halogen atom, or two or more of the plurality of $R^R$s taken together represent a part of a ring structure having 4 to 20 ring atoms constituted together with the carbon chain to which the two or more of the plurality of $R^R$s bond; and h is an integer of 1 to 11, wherein g+h is no greater than 11.

$R^P$ represents, in light of a degree of copolymerization of a monomer that gives the structural unit (III), preferably a hydrogen atom or a methyl group, and more preferably a hydrogen atom.

$R^Q$ represents preferably a single bond or —COO—.

Examples of the arene having 6 to 20 ring atoms that gives Ar include benzene, naphthalene, anthracene, phenanthrene, tetracene, pyrene. and the like. Of these, benzene or naphthalene is preferred, and benzene is more preferred.

The monovalent organic group having 1 to 20 carbon atoms which may be represented by $R^R$ is exemplified by a monovalent hydrocarbon group having 1 to 20 carbon atoms, a monovalent oxyhydrocarbon group having 1 to 20 carbon atoms, and the like.

Examples of the ring structure having 4 to 20 ring atoms which may be constituted from two or more of the plurality of $R^R$s include alicyclic structures such as a cyclohexane structure and a cyclocyclohexene structure, and the like.

$R^R$ represents preferably an alkyl group, an alkoxy group or a halogen atom, and more preferably a methyl group, a t-butyl group, a methoxy group or a fluorine atom.

In the above formula (4), g is preferably 0 to 2, more preferably 0 or 1, and still more preferably 0.

In the above formula (4), h is preferably 1 to 3, and more preferably 1 or 2.

Examples of the structural unit (III) include structural units (hereinafter, may be also referred to as "structural units (III-1) to (III-14)") represented by the following formulae (4-1) to (4-14), and the like.

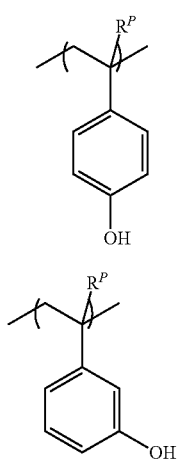

(4-1)

(4-2)

(4-3)

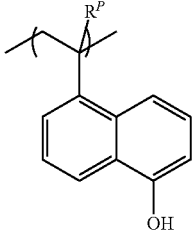

(4-4)

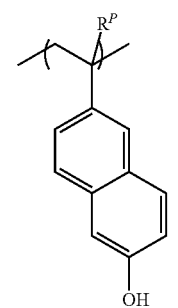

(4-5)

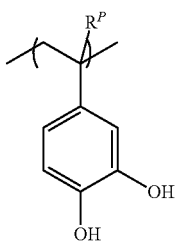

(4-6)

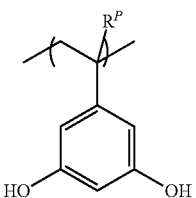

(4-7)

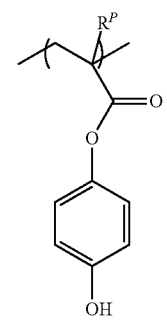

(4-8)

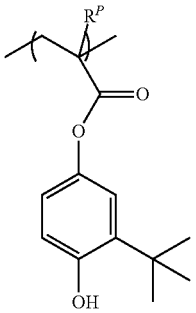

(4-9)

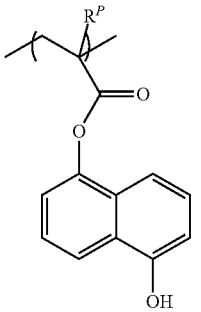

(4-10)

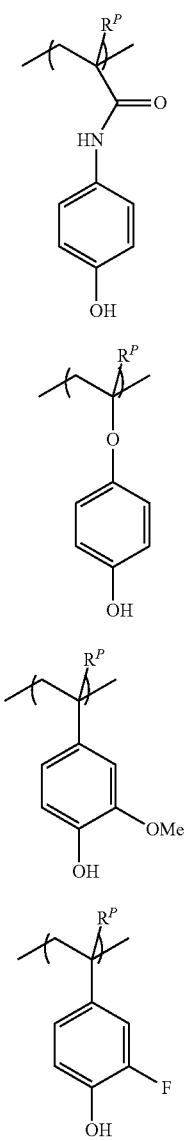

(4-11)

(4-12)

(4-13)

(4-14)

In the above formulae (4-1) to (4-14), $R^P$ is as defined in the above formula (4).

The structural unit (III) is preferably the structural unit (III-1), (III-5), (III-6), (III-8), (III-13) or (III-14).

In a case in which the polymer (A) has the structural unit (III), the lower limit of a proportion of the structural unit (III) contained with respect to the total structural units constituting the polymer (A) is preferably 10 mol %, more preferably 20 mol %, and still more preferably 30 mol %. The upper limit of the proportion of the structural unit (III) is preferably 80 mol %, more preferably 70 mol %, and still more preferably 60 mol %. When the proportion of the structural unit (III) falls within the above range, the sensitivity, the depth of focus and the exposure latitude of the radiation-sensitive resin composition can be further improved.

The structural unit (III) may be formed by, e.g., hydrolyzing in the presence of a base such as triethylamine, a polymer obtained by using a monomer such as, for example, an acyloxystyrene such as acetoxystyrene.

Other Structural Units

The polymer (A) may also have as other structural unit(s), for example, a structural unit that includes an alcoholic hydroxyl group, a structural unit that includes an acid-nonlabile hydrocarbon group, a structural unit that includes a polar group, or the like. Examples of the polar group include a carboxy group, a cyano group, a nitro group, a sulfonamide group, and the like. When the polymer (A) has the structural unit that includes an alcoholic hydroxyl group, the structural unit that includes an acid-nonlabile hydrocarbon group, and/or the structural unit that includes a polar group, the solubility of the resist film into a developer solution can be more adequately adjusted, and as a result, the sensitivity, the depth of focus and the exposure latitude of the radiation-sensitive resin composition can be further improved.

Examples of the structural unit that includes an alcoholic hydroxyl group include structural units represented by the following formulae, and the like.

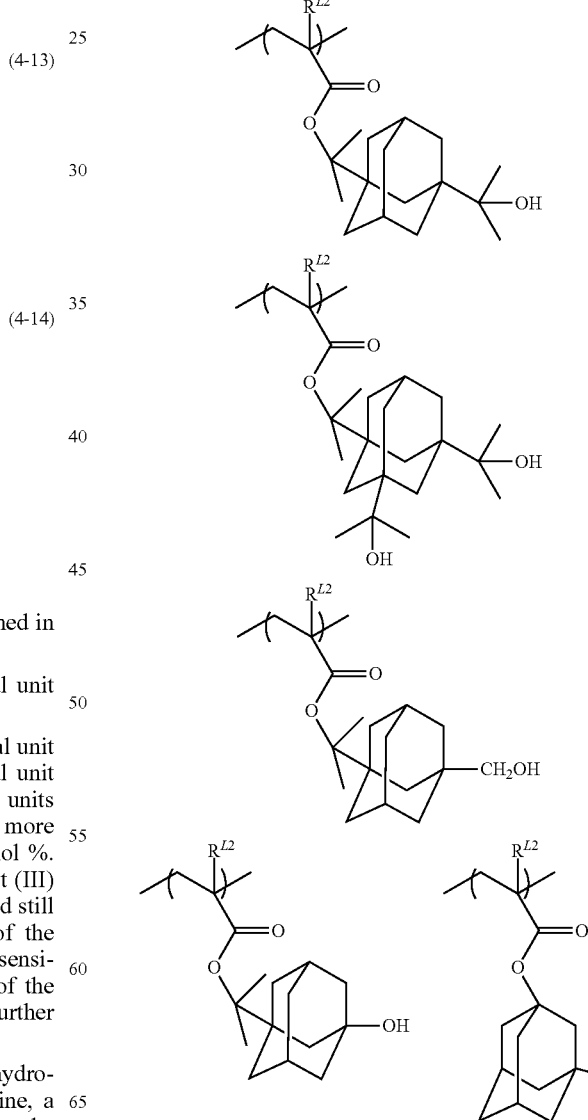

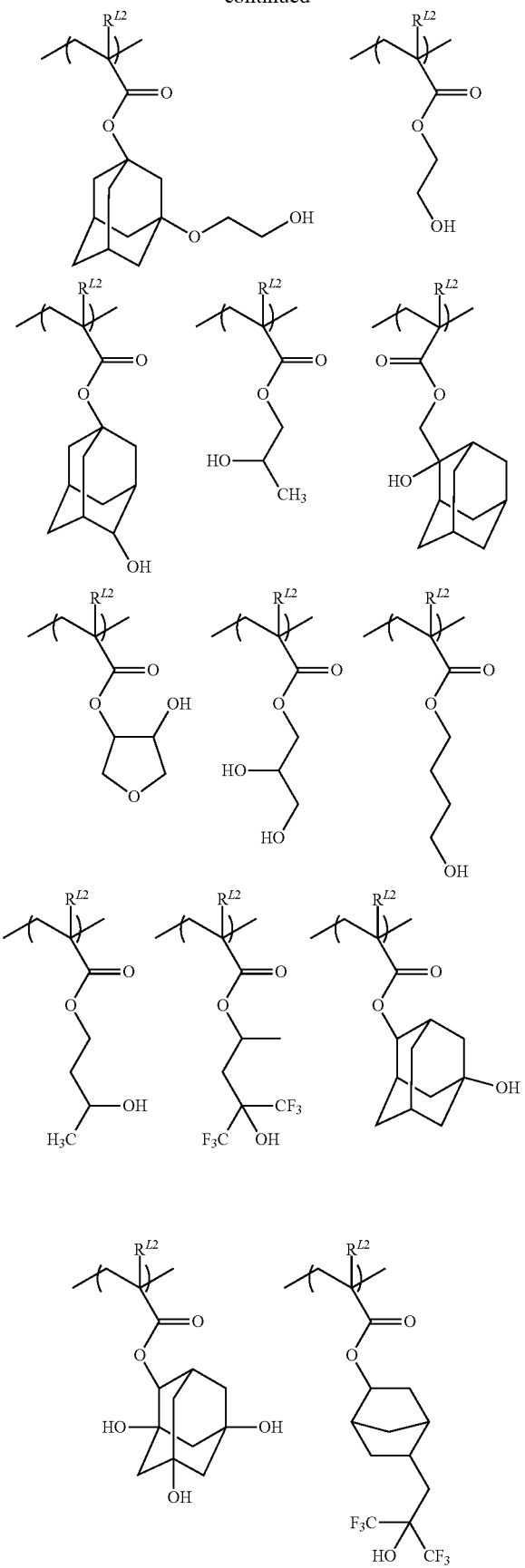
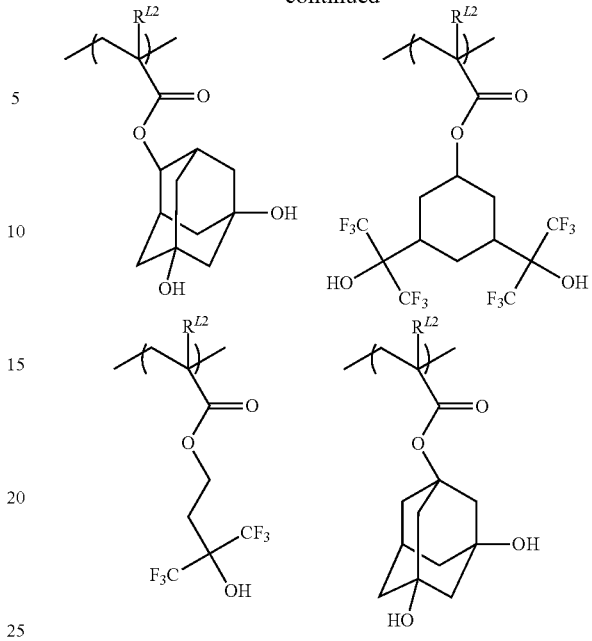

In the above formulae, $R^{L2}$ represents a hydrogen atom, a fluorine atom, a methyl group, or a trifluoromethyl group.

Examples of the structural unit that includes an acid-nonlabile hydrocarbon group include: structural units derived from (meth)acrylic acid primary alkyl esters such as butyl (meth)acrylate; structural units derived from (meth)acrylic acid secondary alkyl esters such as cyclohexyl (meth)acrylate; structural units derived from (meth)acrylic acid aryl esters such as phenyl (meth)acrylate; structural units derived from vinyl aromatic hydrocarbons such as styrene, vinylnaphthalene and vinylpyrene; and the like.

In the case in which the polymer (A) has the other structural unit(s), the lower limit of a proportion of the other structural unit(s) contained with respect to the total structural units constituting the polymer (A) is preferably 1 mol %, more preferably 5 mol %, and still more preferably 10 mol %. The upper limit of the proportion of the other structural unit(s) is preferably 50 mol %, more preferably 35 mol %, and still more preferably 20 mol %.

The lower limit of the content of the polymer (A) with respect to all components of the radiation-sensitive resin composition other than the solvent (E) is preferably 50% by mass, more preferably 65% by mass, and still more preferably 75% by mass. The upper limit of the content is preferably 99% by mass, and more preferably 90% by mass. One, or two or more types of the polymer (A) may be contained.

Synthesis Method of Polymer (A)

The polymer (A) may be synthesized by, for example, polymerizing monomers that give the structural unit (I), and as needed, the structural units (II), (III) and the other structural(s) unit by using a radical polymerization initiator or the like in a solvent.

The lower limit of a polystyrene-equivalent weight average molecular weight (Mw) of the polymer (A) as determined by gel permeation chromatography (GPC) is preferably 1,000, more preferably 4,000, still more preferably 5,000, and particularly preferably 6,000. The upper limit of the Mw is preferably 100,000, more preferably 50,000, still more preferably 20,000, and particularly preferably 8,000.

When the Mw of the polymer (A) falls within the above range, coating characteristics of the radiation-sensitive resin composition can be improved.

The upper limit of the ratio (Mw/Mn) of the Mw to a polystyrene equivalent number average molecular weight (Mn) as determined by GPC of the polymer (A) is preferably 5, more preferably 3, still more preferably 2, and particularly preferably 1.7. The lower limit of the ratio is typically 1, and preferably 1.2.

The Mw and the Mn of the polymer as referred to herein are values determined by using gel permeation chromatography (GPC) under the following conditions.

GPC columns: Tosoh Corporation, "G2000 HXL"×2; "G3000 HXL"×1; and "G4000 HXL"×1
column temperature: 40° C.
elution solvent: tetrahydrofuran (FUJIFILM Wako Pure Chemical Corporation)
flow rate: 1.0 mL/min
sample concentration: 1.0% by mass
amount of injected sample: 100 μL
detector: differential refractometer
standard substance: mono-dispersed polystyrene (B) Acid Generating Agent The acid generating agent (B) is a compound that includes a sulfonate anion (hereinafter, may be also referred to as "anion (W)") and a radiation-sensitive cation (hereinafter, may be also referred to as "cation (X)"). In the acid generating agent (B), the anion (W) has two or more rings (hereinafter, may be also referred to as "rings (A)"). Furthermore, an iodine atom and a monovalent group having 0 to 10 carbon atoms (hereinafter, may be also referred to as "group (I)") which includes at least one of an oxygen atom and a nitrogen atom are bonded to at least one of the rings (A).

Anion (W)

The anion (W) is a sulfonate anion having two or more rings (A), with an iodine atom and the group (I) being bonded to at least one of the rings (A).

The ring (A) is exemplified by an aromatic ring having 6 to 20 ring atoms (aromatic carbon ring), an alicyclic ring having 3 to 20 ring atoms (aliphatic carbon ring), an aromatic heterocyclic ring having 5 to 20 ring atoms, an aliphatic heterocyclic ring having 3 to 20 ring atoms, and the like.

Examples of the aromatic ring include a benzene ring, a naphthalene ring, an anthracene ring, a phenanthrene ring, a tetracene ring, a pyrene ring, and the like.

Examples of the aliphatic ring include: monocyclic saturated aliphatic rings such as a cyclopropane ring, a cyclobutane ring, a cyclopentane ring, a cyclohexane ring, a cycloheptane ring, a cyclooctane ring and a cyclodecane ring; polycyclic saturated aliphatic rings such as a norbornane ring, an adamantane ring, a tricyclodecane ring and a tetracyclododecane ring; monocyclic unsaturated aliphatic rings such as a cyclopentene ring and a cyclohexene ring; polycyclic unsaturated aliphatic rings such as a norbornene ring, a tricyclodecene ring and a tetracyclododecene ring; and the like.

Examples of the aromatic heterocyclic ring include a furan ring, a pyrrole ring, a thiophene ring, a pyran ring, a pyridine ring, a pyrazine ring, a pyrimidine ring, a benzofuran ring, an indole ring, a benzothiophene ring, and the like.

Examples of the aliphatic heterocyclic ring include a tetrahydrofuran ring, a pyrrolidine ring, a piperidine ring, a piperazine ring, a morpholine ring, a 1,3-dioxolane ring, a 1,4-dioxaspiro[4.5]decane ring, a 3,5-dioxatricyclo[5.2.1.0$^{2,6}$]decane ring, and the like.

The ring (A) is preferably the aromatic ring, the aliphatic ring or the aliphatic heterocyclic ring, and more preferably a benzene ring, a naphthalene ring, a cyclohexane ring, a norbornane ring, an adamantane ring, a 1,3-dioxolane ring or a 1,4-dioxaspiro[4.5]decane ring.

The number of the rings (A) in the anion (W) is preferably 2 to 10, more preferably 2 to 5, still more preferably 2 to 4, and particularly preferably 2 or 3.

The number of carbon atoms of the group (I) is preferably 0 to 8, more preferably 0 to 6, still more preferably 0 to 4, particularly preferably 0 to 3, further particularly preferably 0 to 2, and most preferably 0 or 1.

The group (I) is exemplified by a hydroxy group, a hydroxyhydrocarbon group, a group that includes a lactone structure, a group that includes a cyclic carbonate structure, a group that includes a sultone structure, an acyl group, an acyloxy group, a carbonyloxyhydrocarbon group, an oxyhydrocarbon group, an amino group, an aminohydrocarbon group, a group that includes a lactam structure, a group that includes a cyclic carbamate structure, a group that includes a cyclic urea structure, a group that includes a sultam structure, an oxime group (—C=N—OH), a nitro group, and the like. The "amino group" as referred to may include —NH$_2$, as well as —NHR, —NR$_2$ (wherein R represents a monovalent hydrocarbon group) and a cyclic amino group such as a piperidino group.

Examples of a monovalent hydroxyhydrocarbon group include: hydroxyalkyl groups such as a hydroxymethyl group and a hydroxyethyl group; hydroxycycloalkyl groups such as a hydroxycyclohexyl group; hydroxyaryl groups such as a hydroxyphenyl group and a hydroxynaphthyl group; hydroxyaralkyl groups such as a hydroxybenzyl group; and the like.

Examples of a monovalent group that includes a lactone structure include a γ-butyrolactone-yl group, a γ-butyrolactone-yloxycarbonyl group, a norbornane-2,6-lactone-yl group, a norbornane-2,6-lactone-yloxycarbonyl group, and the like.

Examples of a monovalent group that includes a cyclic carbonate structure include an ethylene carbonate-yl group, an ethylene carbonate-ylmethyl group, an ethylene carbonate-ylmethyloxycarbonyl group, a cyclohexenecarbonate-ylmethyloxycarbonyl group, and the like.

Examples of a monovalent group that includes a sultone structure include a norbornane-2,6-sultone-yl group, a norbornane-2,6-sultone-yloxycarbonyl group, and the like.

Examples of the acyl group include a formyl group, an acetyl group, a propionyl group, a butyryl group, a cyclohexylcarbonyl group, a benzoyl group, and the like.

Examples of the acyloxy group include a formyloxy group, an acetoxy group, a propionyloxy group, a butyryloxy group, a cyclohexylcarbonyloxy group, a benzoyloxy group, and the like.

Examples of a monovalent carbonyloxyhydrocarbon group include: alkoxycarbonyl groups such as a methoxycarbonyl group and an ethoxycarbonyl group; cycloalkyloxycarbonyl groups such as a cyclohexyloxy carbonyl group and a 1-methylcyclohexan-1-yloxycarbonyl group; aryloxycarbonyl groups such as a phenoxy carbonyl group; aralkyloxycarbonyl groups such as a benzyloxycarbonyl group; and the like.

Examples of a monovalent oxyhydrocarbon group include: alkoxy groups such as a methoxy group and an ethoxy group; cycloalkyloxy groups such as a cyclohexyloxy group; aryloxy groups such as a phenoxy group; aralkyloxy groups such as a benzyloxy group; and the like.

Examples of a monovalent aminohydrocarbon group include: aminoalkyl groups such as an aminomethyl group and an aminoethyl group; aminocycloalkyl groups such as an aminocyclohexyl group: aminoaryl groups such as an aminophenyl group; aminoaralkyl groups such as an aminobenzyl group; and the like.

Examples of a monovalent group that includes a lactam structure include a 4-butano-4-lactam-yl group, a 4-butano-4-lactam-yloxycarbonyl group, and the like.

Examples of a monovalent group that includes a cyclic carbamate structure include an ethylene carbamate-yl group, an ethylene carbamate-yloxycarbonyl group, and the like.

Examples of a monovalent group that includes a cyclic urea structure include a 2-imidazolidinone-yl group, a 2-imidazolidinone-yloxycarbonyl group, and the like.

Examples of a monovalent group that incudes a sultam structure include a norbornane-2,6-sultam-yl group, a norbornane-2,6-sultam-yloxycarbonyl group, and the like.

The group (I) is preferably a hydroxy group, the hydroxyhydrocarbon group, the group that includes a lactone structure, the acyl group or the carbonyloxyhydrocarbon group.

The number of iodine atoms in the anion (W) is preferably 1 to 10, more preferably 1 to 5, still more preferably 1 to 3, and particularly preferably 1 or 2.

The group (I) and an iodine atom are bonded to at least one of the rings (A). The group (I) and the iodine atom are each bonded to an atom constituting the ring (A). The atom constituting the ring (A) is preferably a carbon atom.

The number of the group(s) (I) on the ring (A) to which the group (I) and the iodine atom are bonded is preferably 1 to 10, more preferably 1 to 5, still more preferably 1 to 3, and particularly preferably 1 or 2.

The number of the iodine atom(s) on the ring (A) to which the group (I) and the iodine atom are bonded is preferably 1 to 10, more preferably 1 to 5, still more preferably 1 to 3, and particularly preferably 1 or 2.

The ring (A) to which the group (I) and the iodine atom are bonded is preferably the aromatic ring or the aliphatic ring, and more preferably the aromatic ring.

To the ring (A) to which the group (I) and the iodine atom are bonded, other group(s) (hereinafter, may be also referred to as "group (II)") aside from the group (I) and the iodine atom may be bonded. The group (II) is exemplified by a monovalent hydrocarbon group having 1 to 20 carbon atoms, a monovalent halogenated hydrocarbon group having 1 to 20 carbon atoms, a halogen atom, and the like.

The anion (W) preferably has a carbon chain adjacent to a sulfur atom of —$SO_3^-$, and it is more preferred that a fluorine atom is bonded to the carbon chain.

Cation (X)

The cation (X) is a radiation-sensitive cation. The cation (X) is preferably a radiation-sensitive onium cation. The cation (X) may be monovalent, or divalent or multivalent, but a monovalent cation is preferred.

Examples of the monovalent radiation-sensitive onium cation include a cation (hereinafter, may be also referred to as "cation (X-1)") represented by the following formula (X-1), a cation (hereinafter, may be also referred to as "cation (X-2)") represented by the following formula (X-2), a cation (hereinafter, may be also referred to as "cation (X-3)") represented by the following formula (X-3), and the like.

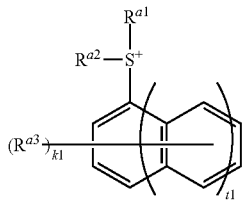

(X-1)

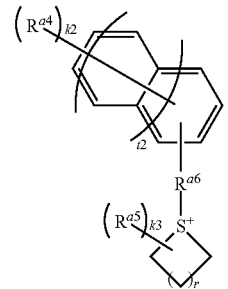

(X-2)

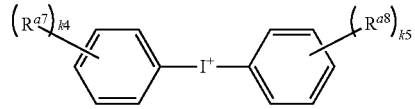

(X-3)

In the above formula (X-1), $R^{a1}$ and $R^{a2}$ each independently represent a monovalent organic group having 1 to 20 carbon atoms; k1 is an integer of 0 to 5, wherein in a case in which k1 is 1, $R^{a3}$ represents a monovalent organic group having 1 to 20 carbon atoms, a hydroxy group, an amino group, a nitro group, a thiol group or a halogen atom, or in a case in which k1 is no less than 2, a plurality of $R^{a3}$s are identical or different from each other and each represents a monovalent organic group having 1 to 20 carbon atoms, a hydroxy group, an amino group, a nitro group, a thiol group or a halogen atom, or the plurality of $R^{a3}$s taken together represent a part of a ring structure having 4 to 20 ring atoms constituted together with the carbon chain to which the plurality of $R^{a3}$s bond; and t1 is an integer of 0 to 3.

In the above formula (X-2), k2 is an integer of 0 to 7, wherein in a case in which k2 is 1, $R^{a4}$ represents a monovalent organic group having 1 to 20 carbon atoms, a hydroxy group, an amino group, a nitro group, a thiol group or a halogen atom, or in a case in which k2 is no less than 2, a plurality of $R^{a4}$s are identical or different from each other and each represents a monovalent organic group having 1 to 20 carbon atoms, a hydroxy group, an amino group, a nitro group, a thiol group or a halogen atom, or the plurality of $R^{a4}$s taken together represent a part of a ring structure having 4 to 20 ring atoms constituted together with the carbon chain to which the plurality of $Ra^4$s bond; k3 is an integer of 0 to 6, wherein in a case in which k3 is 1, $R^{a5}$ represents a monovalent organic group having 1 to 20 carbon atoms, a hydroxy group, an amino group, a nitro group, a thiol group or a halogen atom, or in a case in which k3 is no less than 2, a plurality of $R^{a5}$s are identical or different from each other and each represents a monovalent organic group having 1 to 20 carbon atoms, a hydroxy group, an amino group, a nitro group, a thiol group or a halogen atom, or the plurality of $R^{a5}$s taken together represent a part of a ring structure having 3 to 20 ring atoms constituted together with the carbon chain to which the plurality of $R^{a5}$s bond; r is an integer of 0 to 3; $R^{a6}$ represents a single bond or a divalent organic group having 1 to 20 carbon atoms; and t2 is an integer of 0 to 2.

In the above formula (X-3), k4 is an integer of 0 to 5, wherein in a case in which k4 is 1, $R^{a7}$ represents a monovalent organic group having 1 to 20 carbon atoms, a hydroxy group, an amino group, a nitro group, a thiol group or a halogen atom, or in a case in which k4 is no less than 2, a plurality of $R^{a7}$s are identical or different from each other and each represents a monovalent organic group having 1 to 20 carbon atoms, a hydroxy group, an amino group, a nitro group, a thiol group or a halogen atom, or the plurality of $R^{a7}$s taken together represent a part of a ring structure having 4 to 20 ring atoms constituted together with the carbon chain to which the plurality of $R^{a7}$s bond; and k5 is an integer of 0 to 5, wherein in a case in which k5 is 1, $R^{a8}$ represents a monovalent organic group having 1 to 20 carbon atoms, a hydroxy group, an amino group, a nitro group, a thiol group or a halogen atom, or in a case in which k5 is no less than 2, a plurality of $R^{a8}$s are identical or different from each other and each represent a monovalent organic group having 1 to 20 carbon atoms, a hydroxy group, an amino group, a nitro group, a thiol group or a halogen atom, or the plurality of $R^{a8}$s taken together represent a part of a ring structure having 4 to 20 ring atoms constituted together with the carbon chain to which the plurality of $R^{a8}$s bond.

Examples of the monovalent organic group having 1 to 20 carbon atoms which may be represented by $R^{a1}$ to $R^{a5}$, $R^{a7}$ or $R^{a8}$ include groups similar to the organic groups exemplified as $R^2$ in the above formula (1), and the like. Examples of the divalent organic group which may be represented by $R^{a6}$ include groups obtained by removing one hydrogen atom from the monovalent organic group having 1 to 20 carbon atoms exemplified as $R^2$ in the above formula (1), and the like. $R^{a6}$ represents, in particular, preferably a single bond or a divalent aromatic hydrocarbon group having 6 to 20 carbon atoms.

Examples of the acid generating agent (B) include a compound represented by the following formula (1) (hereinafter, may be also referred to as "(B1) acid generating agent" or "acid generating agent (B1)"), and the like.

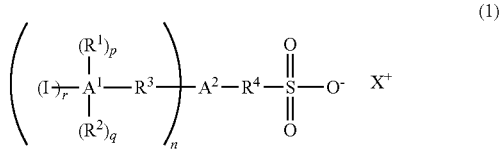

In above formula (1), $A^1$ represents a group obtained from a compound which includes a ring having 3 to 20 ring atoms by removing (p+q+r+1) hydrogen atoms on the ring; $R^1$ represents a monovalent group having 0 to 10 carbon atoms which includes at least one of an oxygen atom and a nitrogen atom; $R^2$ represents a monovalent hydrocarbon group having 1 to 20 carbon atoms, a monovalent halogenated hydrocarbon group having 1 to 20 carbon atoms or a halogen atom; p is an integer of 1 to 10; q is an integer of 0 to 9; r is an integer of 1 to 10, wherein (p+q+r) is no greater than 11; $R^3$ represents a single bond, —O— or —COO—; $A^2$ represents an organic group having a valency of (n+1) and having 3 to 30 carbon atoms that includes a ring having 3 to 20 ring atoms; n is an integer of 1 to 3, wherein in a case in which there exist a plurality of $R^1$s, the plurality of $R^1$ are identical or different from each other; in a case in which there exist a plurality of $R^2$s, the plurality of $R^2$s are identical or different from each other, and wherein in a case in which n is no less than 2, a plurality of $A^1$s are identical or different from each other, a plurality of $R^3$s are identical or different from each other, a plurality of "p"s are identical or different from each other, a plurality of "q"s are identical or different from each other, and a plurality of "r"s are identical or different from each other; $R^4$ represents a fluorinated alkanediyl group having 1 to 10 carbon atoms; and $X^+$ represents a monovalent radiation-sensitive onium cation.

$R^1$, $R^2$ and I (iodine atom) in the above formula (1) are bonded to atoms constituting the ring in A'. The atoms constituting this ring are preferably carbon atoms.

Examples of a compound that includes a ring having 3 to 20 ring atoms that can give $A^1$ include:

compounds each including an aromatic ring having 6 to 20 ring atoms such as benzene, naphthalene, anthracene, phenanthrene, tetracene or pyrene;

compounds each including an aliphatic ring having 3 to 20 ring atoms such as cyclopropane, cyclobutane, cyclopentane, cyclohexane, cycloheptane, cyclooctane, cyclodecane, norbornane, adamantane, tricyclodecane or tetracyclododecane;

compounds each including an aromatic heterocyclic ring having 5 to 20 ring atoms such as furan, pyrrole or thiophene;

compounds each including an aliphatic heterocyclic ring having 3 to 20 ring atoms such as tetrahydrofuran, pyrrolidine, piperidine or tetrahydrothiophene; and the like.

Examples of the monovalent group having 0 to 10 carbon atoms which includes at least one of an oxygen atom and a nitrogen atom and which is represented by $R^1$ include the aforementioned group (I), and the like.

It is preferred that $R^1$ represents a hydroxy group, a hydroxyhydrocarbon group, a group that includes a lactone structure, an acyl group, or a carbonyloxyhydrocarbon group.

Examples of the monovalent hydrocarbon group having 1 to 20 carbon atoms which may be represented by $R^2$ include groups similar to the monovalent hydrocarbon groups having 1 to 20 carbon atoms exemplified as $R^X$ to $R^W$ in the above formulae (2-1A) to (2-2B), and the like.

Examples of the monovalent halogenated hydrocarbon group having 1 to 20 carbon atoms which may be represented by $R^2$ include groups obtained by substituting with a halogen atom a part or all of hydrogen atoms included in a monovalent hydrocarbon group having 1 to 20 carbon atoms exemplified as $R^X$ to $R^W$ in the above formulae (2-1A) to (2-2B), and the like.

Examples of the halogen atom which may be represented by $R^2$ include a fluorine atom, a chlorine atom, a bromine atom, and the like.

$R^2$ represents preferably the hydrocarbon group, more preferably an alkyl group, and still more preferably a methyl group.

It is preferred that p is 1 to 5, and p is more preferably 1 to 3 and still more preferably 1 or 2.

It is preferred that q is 0 to 3, and q is more preferably 0 to 2 and still more preferably 0 or 1.

It is preferred that r is 1 to 5, and r is more preferably 1 to 3 and still more preferably 1 or 2.

$R^3$ represents preferably —COO—.

The organic group having a valency of (n+1) and having 3 to 30 carbon atoms that includes a ring having 3 to 20 ring atoms represented by $A^2$ is exemplified by: a hydrocarbon group having a valency of (n+1) and having 3 to 20 ring atoms; a group (a) that includes a divalent hetero atom-containing group between two adjacent carbon atoms of this hydrocarbon group; a group (β) obtained by substituting with a monovalent hetero atom-containing group a part or all of hydrogen atoms included in the hydrocarbon group or the group (α); a group (γ) obtained by combining the hydrocarbon group, the group (α) or the group (β) with a divalent hetero atom-containing group; and the like.

Examples of the hydrocarbon group having a valency of (n+1) and having 3 to 30 ring atoms include groups similar to groups obtained by removing n hydrogen atom(s) on an aliphatic ring or on an aromatic ring included in the monovalent alicyclic hydrocarbon group having 3 to 20 carbon atoms or the monovalent aromatic hydrocarbon group having 6 to 20 carbon atoms exemplified as $R^X$ to $R^W$ in the above formulae (2-1A) to (2-2B), and the like.

Examples of the hetero atom that may constitute the divalent or monovalent hetero atom-containing group include an oxygen atom, a nitrogen atom, a sulfur atom, a phosphorus atom, a silicon atom, and the like.

Examples of the divalent hetero atom-containing group include —O—, —CO—, —S—, —CS—, —NR'—, groups obtained by combining at least two of the aforementioned groups, and the like, wherein R' represents a hydrogen atom or a monovalent chain hydrocarbon group. Of these, —COO—, —O— or —S— is preferred, and —COO— is more preferred.

Examples of the monovalent hetero atom-containing group include a hydroxy group, a carboxy group, a cyano group, an amino group, a sulfanyl group, and the like.

The ring in $A^2$ is preferably an aromatic ring, an aliphatic ring, an aliphatic heterocyclic ring, an aromatic ring and an aliphatic ring, an aromatic ring and an aliphatic heterocyclic ring, or an aliphatic ring and an aliphatic heterocyclic ring, and more preferably a benzene ring, a naphthalene ring, a cyclohexane ring, a norbornane ring, an adamantane ring, a 1,3-dioxolane ring, a 1,4-dioxaspiro[4.5]decane ring, a benzene ring and a norbornane ring, a benzene ring and a 1,3-dioxolane ring, a benzene ring and a 1,4-dioxaspiro[4.5]decane ring, or a norbornane ring and a 1,3-dioxolane ring.

In the case in which n is 1, $A^2$ is preferably a group represented by -$A^{2'}$-*, -$A^{2''}$—COO—* or -$A^{2''}$—OCO—* (wherein $A^{2'}$ represents a divalent organic group having 3 to 30 carbon atoms that includes a ring having 3 to 20 ring atoms; $A^{2''}$ represents a divalent organic group having 3 to 29 carbon atoms that includes a ring having 3 to 20 ring atoms; and *denotes a site to be bonded to $R^4$ in the above formula (1)).

In the above formula, n is preferably 1 or 2, and more preferably 1.

Examples of the fluorinated alkanediyl group having 1 to 10 carbon atoms represented by $R^4$ include a fluoromethanediyl group, a difluoromethanediyl group, a 1,1-difluoroethane-1,2-diyl group, a 2,2-difluoroethane-1,2-diyl group, a 1,1,2-trifluoroethane-1,2-diyl group, a 1,1,2,2-tetrafluoroethane-1,2-diyl group, a 1,1,3,3,3-pentafluoropropane-1,2-diyl group, a 1,1,2,2-tetrafluoropentane-1,5-diyl group, a 3,3,3-trifluoropropane-1,2-diyl group, and the like.

$R^4$ is preferably a group represented by the following formula (F).

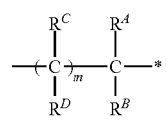

In the above formula (F), $R^A$ and $R^B$ each independently represent a hydrogen atom or a fluorine atom; $R^C$ and $R^D$ each independently represent a hydrogen atom, a fluorine atom or a perfluoroalkyl group having 1 to 10 carbon atoms; m is an integer of 0 to 3, wherein in a case in which m is no less than 2, a plurality of $R^C$s are identical or different from each other and a plurality of $R^D$s are identical or different from each other, and wherein at least one of $R^A$, $R^B$, one or a plurality of $R^C$s and one or a plurality of $R^D$s represents a fluorine atom or a perfluoroalkyl group; and * denotes a site to be bonded to a sulfur atom of —S(=O)$_2$—O$^-$ in the above formula (1).

It is preferred that $R^A$ and $R^B$ each represent a fluorine atom.

Examples of the perfluoroalkyl group having 1 to 10 carbon atoms which may be represented by $R^C$ or $R^D$ include a trifluoromethyl group, a pentafluoroethyl group, and the like.

In the above formula, m is preferably 0 to 2, and more preferably 0 or 1.

Examples of the monovalent radiation-sensitive onium cation represented by $X^+$ include the cations (X-1), (X-2) and (X-3) described above, and the like.

Examples of the acid generating agent (B1) include compounds (hereinafter, may be also referred to as "acid generating agents (1-1) to (1-13)") represented by the following formulae (1-1) to (1-13), and the like.

-continued
(1-3)
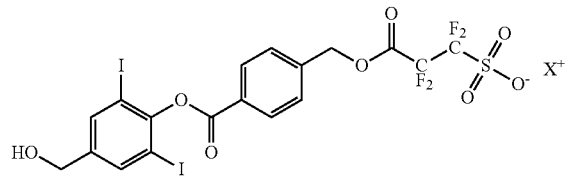
(1-4)
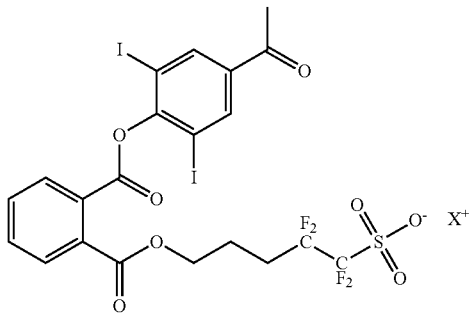
(1-5)
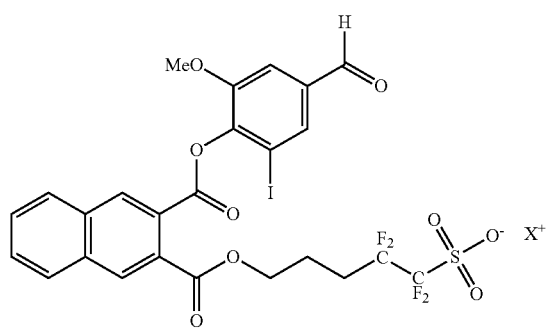
(1-6)
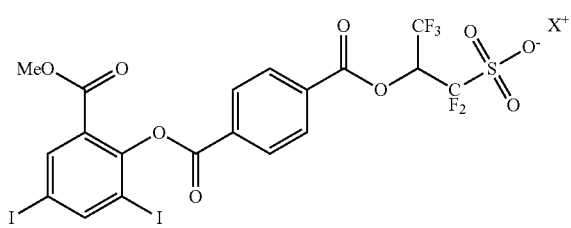
(1-7)
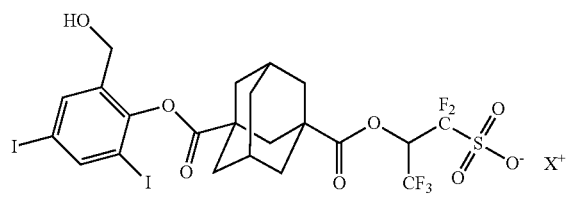
(1-8)
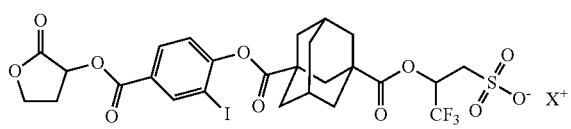
(1-9)
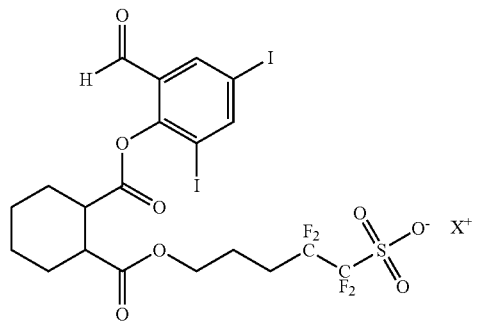
(1-10)
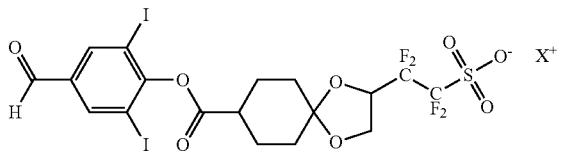
(1-11)
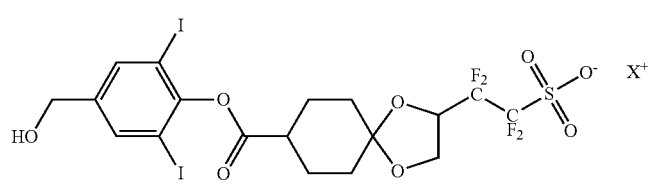

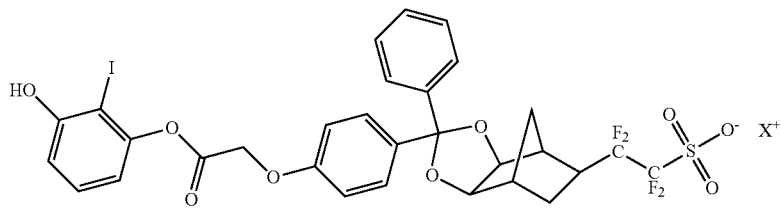
(1-12)

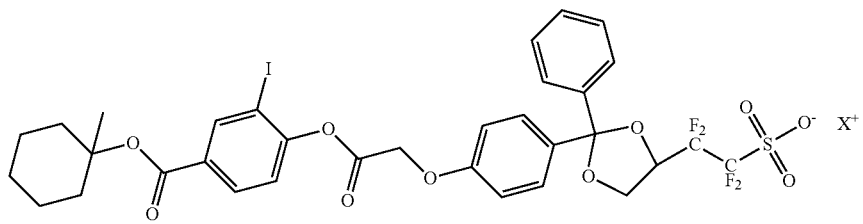
(1-13)

In the above formulae (1-1) to (1-13), $X^+$ is as defined in the above formula (1).

As the acid generating agent (B1), the acid generating agents (1-1) to (1-13) are preferred.

The lower limit of a content of the acid generating agent (B) with respect to 100 parts by mass of the polymer (A) is preferably 0.1 parts by mass, more preferably 1 part by mass, still more preferably 5 parts by mass, particularly preferably 10 parts by mass, further particularly preferably 15 parts by mass, and most preferably 18 parts by mass. The upper limit of the content is preferably 50 parts by mass, more preferably 40 parts by mass, still more preferably 35 parts by mass, and particularly preferably 30 parts by mass. When the content of the acid generating agent (B) falls within the above range, the sensitivity, the depth of focus and the exposure latitude can be further improved. One, or two or more types of the acid generating agent (B) may be contained.

Synthesis Method of Acid Generating Agent (B)

In a case in which n in the above formula (1) is 1 and $R^3$ represents —COO—, for example, the acid generating agent (B1) can be synthesized by permitting a reaction in accordance with a well-known method using: a compound that gives HO—$R^4$—$SO_3^-X^+$ and a compound that gives HOOC-$A^{2'}$—COOH; a compound that gives HOOC—$R^4$—$SO_3^-X^+$ and a compound that gives HO-$A^{2'}$—COOH; or a compound that gives $(HO)_2$—$R^4$—$SO_3^-X^+$ and a compound that gives O=$A^{2''}$—COOH (wherein $A^{2'}$ represents a divalent organic group having 3 to 30 carbon atoms that includes a ring having 3 to 20 ring atoms; and $A^{2''}$ represents a trivalent organic group having 3 to 29 carbon atoms that includes a ring having 3 to 20 ring atoms) to provide HOOC-$A^{2-}R^4$—$SO_3^-X^+$ (wherein, $A^2$ represents a divalent organic group having 3 to 30 carbon atoms that includes a ring having 3 to 20 ring atoms), and then allowing a compound thus obtained to react with $(R^1)_p (R^2)_q (I)_r A^1$—OH.

The acid generating agent (B1) in which $R^1$ represents —$CH_2OH$ can be synthesized by providing the acid generating agent (B1) in which $R^1$ represents —CHO, and then reducing this —CHO.

The acid generating agent (B) other than those described above can also be synthesized in accordance with a similar method to the above method.

(C) Acid Diffusion Controller

The acid diffusion controller (C) controls a phenomenon of diffusion of the acid, which was generated from the acid generating agent (B), etc. upon the exposure, in the resist film, whereby the effect of inhibiting unwanted chemical reactions in an unexposed region is exhibited. In addition, the storage stability of the radiation-sensitive resin composition is improved and the resolution thereof as a resist is further improved. Moreover, variation of the line width of the resist pattern caused by variation of post-exposure time delay from the exposure until a development treatment can be suppressed, which enables the radiation-sensitive resin composition with superior process stability to be obtained. The acid diffusion controller (C) may be contained in the radiation-sensitive resin composition in a form of a free compound (hereinafter, may be referred to as "(C) acid diffusion control agent" or "acid diffusion control agent (C)" as appropriate) or in a form incorporated as a part of the polymer (A), the polymer (D) or the like, or may be in both of these forms.

The acid diffusion control agent (C) is exemplified by a nitrogen-containing compound, a photolabile base, and the like. The photolabile base is a compound that is degraded upon an exposure to have lowered basicity.

Examples of the nitrogen-containing compound include: a compound having one nitrogen atom such as monoalkylamine; a compound having two nitrogen atoms such as ethylenediamine; a compound having three or more nitrogen atoms such as polyethylene imine; an amide group-containing compound such as N,N-dimethylacetamide; a urea compound such as 1,1,3,3-tetramethylurea; a nitrogen-containing heterocyclic compound such as N-(undecylcarbonyloxyethyl)morpholine or N-t-butoxycarbonyl-4-hydroxypiperidine; and the like.

Examples of the photolabile base include compounds represented by the following formulae, and the like.

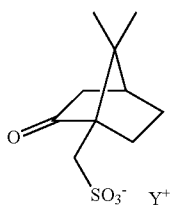 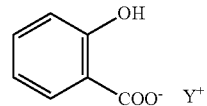

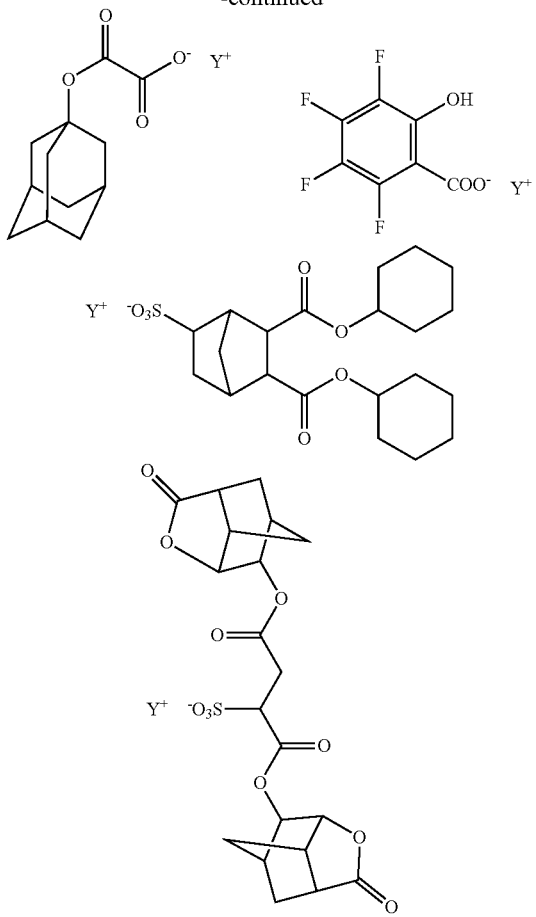

In the above formulae, Y⁺ represents a monovalent radiation-sensitive onium cation.

Examples of the monovalent radiation-sensitive onium cation represented by Y⁺ include cations similar to the cations exemplified as the monovalent radiation-sensitive onium cation represented by X⁺ in the acid generating agent (B), and the like.

In a case in which the radiation-sensitive resin composition contains the acid diffusion control agent (C), the lower limit of a content of the acid diffusion control agent (C) with respect to 100 parts by mass of the polymer (A) is preferably 0.1 parts by mass, more preferably 1 part by mass, and still more preferably 2 parts by mass. The upper limit of the content of the acid diffusion control agent (C) is preferably 30 parts by mass, more preferably 20 parts by mass, and still more preferably 10 parts by mass. The radiation-sensitive resin composition may contain one, or two or more types of the acid diffusion controller (C).

(D) Polymer

The polymer (D) is a polymer having a percentage content by mass of fluorine atoms greater than that of the polymer (A). The polymer (D), having greater hydrophobicity than the polymer (A) as a base resin, tends to be localized in a surface layer of the resist film. As a result, the radiation-sensitive resin composition containing the polymer (D) enables generation of defects on the resist pattern to be inhibited.

The lower limit of a percentage content by mass of fluorine atoms of the polymer (D) is preferably 1% by mass, more preferably 2% by mass, and still more preferably 3% by mass. The upper limit of the percentage content by mass of fluorine atoms of the polymer (D) is preferably 60% by mass, more preferably 50% by mass, and still more preferably 40% by mass. When the percentage content by mass of fluorine atoms falls within the above range, localization of the polymer (D) in the resist film can be more adequately adjusted. It is to be noted that the percentage content by mass of fluorine atoms in the polymer may be determined by ascertaining a structure of the polymer by a $^{13}$C-NMR analysis, and calculating the content based on the structure thereof.

The mode of incorporation of the fluorine atom in the polymer (D) is not particularly limited, and the fluorine atom may bond to any of the main chain, a side chain and an end of the polymer (D); however, the polymer (D) preferably has a structural unit (hereinafter, may be also referred to as "structural unit (F)") that includes a fluorine atom. The polymer (D) may have an other structural unit aside from the structural unit (F).

Examples of the structural unit (F) include a structural unit (hereinafter, may be also referred to as "structural unit (F1)") represented by the following formula (f-1), a structural unit (hereinafter, may be also referred to as "structural unit (F2)") represented by the following formula (f-2), and the like. The structural unit (F) may have one, or two or more types of the structural unit (F1) and the structural unit (F2), respectively.

Structural Unit (F1)

The structural unit (F1) is represented by the following formula (f-1). By virtue of the polymer (D) having the structural unit (F1), the percentage content by mass of fluorine atoms can be adjusted.

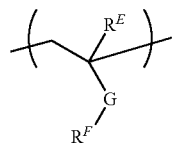

(f-1)

In the above formula (f-1), $R^E$ represents a hydrogen atom, a fluorine atom, a methyl group or a trifluoromethyl group; G represents a single bond, an oxygen atom, a sulfur atom, —COO—, —SO₂NH—, —CONH— or —OCONH—; $R^F$ represents a monovalent fluorinated chain hydrocarbon group having 1 to 6 carbon atoms or a monovalent fluorinated alicyclic hydrocarbon group having 3 to 20 carbon atoms.

In light of a degree of copolymerization of a monomer that gives the structural unit (F1), $R^E$ represents preferably a hydrogen atom or a methyl group, and more preferably a methyl group.

G represents preferably —COO—.

Examples of the monovalent fluorinated chain hydrocarbon group having 1 to 6 carbon atoms which may be represented by $R^F$ include groups obtained by substituting with a fluorine atom a part or all of hydrogen atoms, and the like, these groups being included in the groups exemplified as the monovalent chain hydrocarbon groups having 1 to 6 carbon atoms which may be represented by $R^X$ to $R^W$ in the above formulae (2-1A) to (2-2B), and the like.

Examples of the monovalent fluorinated alicyclic hydrocarbon group having 3 to 20 carbon atoms which may be represented by $R^F$ include groups obtained by substituting with a fluorine atom a part or all of hydrogen atoms, and the like, these groups being included in the groups exemplified as the monovalent alicyclic hydrocarbon groups having 3 to 20 carbon atoms which may be represented by $R^X$ to $R^W$ in the above formulae (2-1A) to (2-2B), and the like.

$R^F$ represents preferably a fluorinated chain hydrocarbon group, more preferably a 2,2,2-trifluoroethyl group or a 1,1,1,3,3,3-hexafluoropropan-2-yl group, and still more preferably a 2,2,2-trifluoroethyl group.

In the case in which the polymer (D) has the structural unit (F1), the lower limit of a proportion of the structural unit (F1) contained with respect to total structural units constituting the polymer (D) is preferably 10 mol %, and more preferably 30 mol %. The upper limit of the proportion is preferably 90 mol %, and more preferably 80 mol %.

Structural Unit (F2)

The structural unit (F2) is represented by the following formula (f-2). Due to having the structural unit (F2), the polymer (D) enables solubility into an alkaline developer solution to be improved.

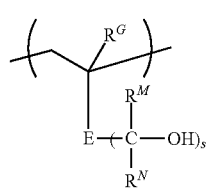

(f-2)

In the above formula (f-2), $R^G$ represents a hydrogen atom, a fluorine atom, a methyl group or a trifluoromethyl group; E represents a single bond or a divalent organic group having 1 to 20 carbon atoms; $R^M$ and $R^N$ each independently represent a fluorine atom or a fluorinated hydrocarbon group having 1 to 10 carbon atoms; and s is an integer of 1 to 3, wherein in a case in which s is no less than 2, a plurality of $R^M$s are identical or different from each other and a plurality of $R^N$s are identical or different from each other.

In light of a degree of copolymerization of a monomer that gives the structural unit (F2), $R^G$ represents preferably a hydrogen atom or a methyl group, and more preferably a methyl group.

Examples of the divalent organic group having 1 to 20 carbon atoms which may be represented by E include —COO—R'— (wherein R' represents a divalent hydrocarbon group having 1 to 19 carbon atoms), and the like.

E represents preferably a divalent organic group having 1 to 20 carbon atoms, and more preferably a carbonyloxynorbornanediyl group or a carbonyloxyethanediyl group.

In a case in which the polymer (D) has the structural unit (F2), the lower limit of a proportion of the structural unit (F2) contained with respect to the total structural units constituting the polymer (D) is preferably 10 mol %, more preferably 20 mol %, and still more preferably 30 mol %. The upper limit of the proportion is preferably 80 mol %, more preferably 70 mol %, and still more preferably 60 mol %.

Other Structural Unit

The other structural unit is exemplified by a structural unit that includes an alcoholic hydroxyl group (except for those corresponding to the structural unit (F2)), and the like. Examples of the structural unit that includes an alcoholic hydroxyl group include structural units exemplified as the structural unit that includes an alcoholic hydroxyl group in the polymer (A), and the like. The structural unit that includes an alcoholic hydroxyl group is preferably a structural unit derived from 3-hydroxyadamantane-1-yl (meth)acrylate.

In a case in which the polymer (D) has the other structural unit, the lower limit of a proportion of the other structural unit contained with respect to the total structural units constituting the polymer (D) is preferably 1 mol %, and more preferably 10 mol %. The upper limit of the proportion is preferably 60 mol %, and more preferably 40 mol %.

In a case in which the radiation-sensitive resin composition contains the polymer (D), the lower limit of a content of the polymer (D) with respect to 100 parts by mass of the polymer (A) is preferably 0.1 parts by mass, more preferably 1 part by mass, still more preferably 2 parts by mass, and particularly preferably 4 parts by mass. The upper limit of the content is preferably 30 parts by mass, more preferably 20 parts by mass, still more preferably 15 parts by mass, and particularly preferably 10 parts by mass. The radiation-sensitive resin composition may contain one, or two or more types of the polymer (D).

The polymer (D) can be synthesized in accordance with a method similar to that of the polymer (A) described above.

The lower limit of the Mw of the polymer (D) as determined by GPC is preferably 1,000, more preferably 3,000, still more preferably 4,000, and particularly preferably 5,000. The upper limit of the Mw is preferably 100,000, more preferably 50,000, still more preferably 20,000, and particularly preferably 8,000. When the Mw of the polymer (D) falls within the above range, the coating characteristics of the radiation-sensitive resin composition can be further improved.

The upper limit of a ratio (Mw/Mn) of the Mw to the Mn of the polymer (D) as determined by GPC is preferably 5, more preferably 3, and still more preferably 2. The lower limit of the ratio is typically 1, and preferably 1.5.

(E) Solvent

The radiation-sensitive resin composition typically contains the solvent (E). The solvent (E) is not particularly limited as long as it is a solvent capable of dissolving or dispersing at least the polymer (A) and the acid generator (B), as well as the optional component which is contained as desired.

The solvent (E) is exemplified by an alcohol solvent, an ether solvent, a ketone solvent, an amide solvent, an ester solvent, a hydrocarbon solvent, and the like.

Examples of the alcohol solvent include:

aliphatic monohydric alcohol solvents having 1 to 18 carbon atoms such as 4-methyl-2-pentanol and n-hexanol;

alicyclic monohydric alcohol solvents having 3 to 18 carbon atoms such as cyclohexanol;

polyhydric alcohol solvents having 2 to 18 carbon atoms such as 1,2-propylene glycol;

polyhydric alcohol partial ether solvents having 3 to 19 carbon atoms such as propylene glycol monomethyl ether; and the like.

Examples of the ether solvent include:

dialkyl ether solvents such as diethyl ether, dipropyl ether, dibutyl ether, dipentyl ether, diisoamyl ether, dihexyl ether and diheptyl ether;

cyclic ether solvents such as tetrahydrofuran and tetrahydropyran;

aromatic ring-containing ether solvents such as diphenyl ether and anisole; and the like.

Examples of the ketone solvent include:

chain ketone solvents such as acetone, methyl ethyl ketone, methyl n-propyl ketone, methyl n-butyl ketone, diethyl ketone, methyl iso-butyl ketone, 2-heptanone, ethyl n-butyl ketone, methyl n-hexyl ketone, di-iso-butyl ketone and trimethylnonanone;

cyclic ketone solvents such as cyclopentanone, cyclohexanone, cycloheptanone, cyclooctanone and methylcyclohexanone;

2,4-pentanedione, acetonylacetone and acetophenone; and the like.

Examples of the amide solvent include:

cyclic amide solvents such as N,N'-dimethylimidazolidinone and N-methylpyrrolidone;

chain amide solvents such as N-methylformamide, N,N-dimethylformamide, N,N-diethylformamide, acetamide, N-methylacetamide, N,N-dimethylacetamide and N-methylpropionamide; and the like.

Examples of the ester solvent include:

monocarboxylic acid ester solvents such as n-butyl acetate and ethyl lactate;

polyhydric alcohol carboxylate solvents such as propylene glycol acetate;

polyhydric alcohol partial ether carboxylate solvents such as propylene glycol monomethyl ether acetate;

polyhydric carboxylic acid diester solvents such as diethyl oxalate; carbonate solvents such as dimethyl carbonate and diethyl carbonate; and the like.

Examples of the hydrocarbon solvent include:

aliphatic hydrocarbon solvents having 5 to 12 carbon atoms such as n-pentane and n-hexane;

aromatic hydrocarbon solvents having 6 to 16 carbon atoms such as toluene and xylene; and the like.

Of these, the alcohol solvent and/or the ester solvent are/is preferred, the polyhydric alcohol partial ether solvent and/or the polyhydric alcohol partial ether carboxylate solvent are/is more preferred, and propylene glycol monomethyl ether and/or propylene glycol monomethyl ether acetate are/is still more preferred. One, or two or more types of the solvent (E) may be contained.

Other Optional Components

The other optional component is exemplified by a surfactant and the like. For each of the other optional components, one, or two or more types thereof in combination may be used.

Surfactant

The surfactant achieves the effect of improving the coating characteristics, striation, developability, and the like. Examples of the surfactant include nonionic surfactants such as polyoxyethylene lauryl ether, and the like. In a case in which the radiation-sensitive resin composition contains the surfactant, the upper limit of a content of the surfactant with respect to 100 parts by mass of the polymer (A) is preferably 2 parts by mass.

Preparation Method of Radiation-Sensitive Resin Composition

The radiation-sensitive resin composition may be prepared, for example, by mixing the polymer (A) and the acid generator (B), as well as the other optional component(s) such as the acid diffusion controller (C), the polymer (D) or/and the solvent (E) which is/are added as needed, in a certain ratio, and preferably filtering a thus resulting mixture through a filter or the like having a pore size of about 0.2 The lower limit of a proportion of all components other than the solvent (E) in the radiation-sensitive resin composition is preferably 0.1% by mass, more preferably 0.5% by mass, and still more preferably 1% by mass. The upper limit of the proportion of all components other than the solvent (E) is preferably 50% by mass, more preferably 30% by mass, and still more preferably 10% by mass.

The radiation-sensitive resin composition is particularly suited for use in an exposure to EUV and/or use in an exposure to an electron beam.

Resist Pattern-Forming Method

The resist pattern-forming method according to an embodiment of the present invention includes: a step of applying the radiation-sensitive resin composition according to the embodiment of the invention directly or indirectly on at least one face side of a substrate (hereinafter, may be also referred to as "applying step"); a step of exposing the resist film formed by the applying step (hereinafter, may be also referred to as "exposing step"); and a step of developing the resist film exposed (hereinafter, may be also referred to as "developing step"). In the resist pattern-forming method, the aforementioned radiation-sensitive resin composition is used as the radiation-sensitive resin composition.

According to the resist pattern-forming method, due to use of the radiation-sensitive resin composition, formation of a resist pattern is enabled with superior sensitivity, depth of focus and exposure latitude. Hereinafter, each step will be described.

Applying Step

In this step, the radiation-sensitive resin composition according to the first embodiment of the invention is applied directly or indirectly on a substrate to thereby form a resist film. The substrate on which the resist film is to be formed is exemplified by a conventionally well-known substrate such as a silicon wafer, a wafer coated with silicon dioxide or aluminum, and the like. In addition, an organic underlayer film such as an organic or inorganic antireflective film disclosed in, for example, Japanese Examined Patent Application, Publication No. H6-12452, Japanese Unexamined Patent Application, Publication No. S59-93448, and the like may be provided on the substrate. An application procedure is exemplified by spin-coating, cast coating, roll-coating, and the like. After the application, prebaking (PB) may be carried out as needed for evaporating the solvent remaining in the coating film. The lower limit of a PB temperature is preferably 60° C., and more preferably 80° C. The upper limit of the PB temperature is preferably 140° C., and more preferably 120° C. The lower limit of a PB time period is preferably 5 sec, and more preferably 10 sec. The upper limit of the PB time period is preferably 600 sec, and more preferably 300 sec. The lower limit of an average thickness of the resist film formed is preferably 10 nm, and more preferably 20 nm. The upper limit of the average thickness is preferably 1,000 nm, and more preferably 500 nm.

Exposing Step

In this step, the resist film formed by the applying step is exposed. This exposure is carried out by irradiation with an exposure light through a photomask (as the case may be, through a liquid immersion medium such as water). Examples of the exposure light include electromagnetic waves such as visible light rays, ultraviolet rays, far ultraviolet rays, extreme ultraviolet rays (EUV), X-rays and γ-rays; charged particle rays such as electron beams and α-rays, and the like, which may be selected in accordance with a line width of the intended pattern. Of these, far ultraviolet rays, EUV or electron beams are preferred; an ArF excimer laser beam (wavelength: 193 nm), a KrF excimer laser beam (wavelength: 248 nm), EUV or an electron beam is more preferred; and EUV or an electron beam is still more preferred. The resist pattern-forming method is particularly advantageous in the cases of exposure to EUV and exposure to an electron beam since the radiation-sensitive resin composition containing the acid generating agent (B) described above is used.

It is preferred that post exposure baking (PEB) is carried out after the exposure to promote dissociation of the acid-labile group included in the polymer (A), etc. mediated by the acid generated from the acid generating agent (B), etc. upon the exposure in exposed regions of the resist film. This PEB enables an increase in a difference in solubility of the resist film in a developer solution between the light-exposed regions and light-unexposed regions. The lower limit of the PEB temperature is preferably 50° C., and more preferably 80° C. The upper limit of the PEB temperature is preferably 180° C., and more preferably 130° C. The lower limit of the PEB time period is preferably 5 sec, and more preferably 10 sec. The upper limit of the PEB time period is preferably 600 sec, and more preferably 300 sec.

Developing Step

In this step, the resist film exposed is developed. Accordingly, formation of a predetermined resist pattern is enabled. After the development, washing with a rinse agent such as water or an alcohol and then drying is typical. The development procedure in the developing step may be carried out by either development with an alkali, or development with an organic solvent.

In the case of the development with an alkali, the developer solution for use in the development is exemplified by alkaline aqueous solutions prepared by dissolving at least one alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo-[5.4.0]-7-undecene, 1,5-diazabicyclo-[4.3.0]-5-nonene, etc., and the like. Of these, an aqueous TMAH solution is preferred, and a 2.38% by mass aqueous TMAH solution is more preferred.

In the case of the development with an organic solvent, the developer solution is exemplified by: an organic solvent such as a hydrocarbon solvent, an ether solvent, an ester solvent, a ketone solvent and an alcohol solvent; a solution containing the organic solvent; and the like. An exemplary organic solvent includes one, or two or more types of the solvents exemplified as the solvent (E) for the radiation-sensitive resin composition, and the like. Of these, the ester solvent or the ketone solvent is preferred. The ester solvent is preferably an acetic acid ester solvent, and more preferably n-butyl acetate. The ketone solvent is preferably a chain ketone, and more preferably 2-heptanone. The lower limit of the content of the organic solvent in the developer solution is preferably 80% by mass, more preferably 90% by mass, still more preferably 95% by mass, and particularly preferably 99% by mass. Components other than the organic solvent in the organic solvent developer solution are exemplified by water, silicon oil, and the like.

Examples of the development procedure include: a dipping procedure in which the substrate is immersed for a given time period in the developer solution charged in a container; a puddle procedure in which the developer solution is placed to form a dome-shaped bead by way of the surface tension on the surface of the substrate for a given time period to conduct a development; a spraying procedure in which the developer solution is sprayed onto the surface of the substrate; a dynamic dispensing procedure in which the developer solution is continuously applied onto the substrate, which is rotated at a constant speed, while scanning with a developer solution-application nozzle at a constant speed; and the like.

EXAMPLES

Hereinafter, the present invention is explained in detail by way of Examples, but the present invention is not in any way limited to these Examples. Measuring methods for various types of physical properties are shown below.

Measurements of Weight Average Molecular Weight (Mw), Number Average Molecular Weight (Mn) and Dispersity Index (Mw/Mn)

Measurements were carried out by gel permeation chromatography (GPC) using GPC columns available from Tosoh Corporation ("G2000 HXL"×2, "G3000 HXL"×1 and "G4000 HXL"×1) under an analytical conditions involving a flow rate of 1.0 mL/min, an elution solvent of tetrahydrofuran and a column temperature of 40° C., with mono-dispersed polystyrene as a standard.

$^{13}$C-NMR Analysis

Measurement was carried out by using "JNM-Delta400" available from JEOL, Ltd.

Synthesis of Polymer

Monomers used for synthesizing the polymer (A) and the polymer (D) are presented below. It is to be noted that in the following Synthesis Examples, unless otherwise specified particularly, "parts by mass" means a value, provided that the total mass of the monomers used was 100 parts by mass, and "mol %" means a value, provided that the total mol number of the monomers used was 100 mol %.

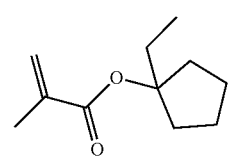

(M-1)

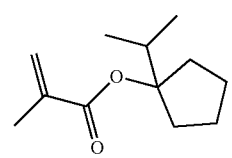

(M-2)

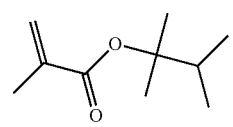

(M-3)

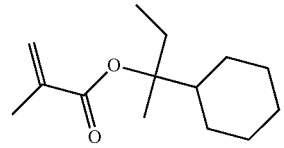

(M-4)

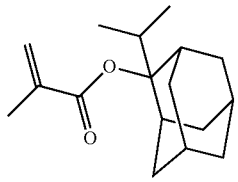

(M-5)

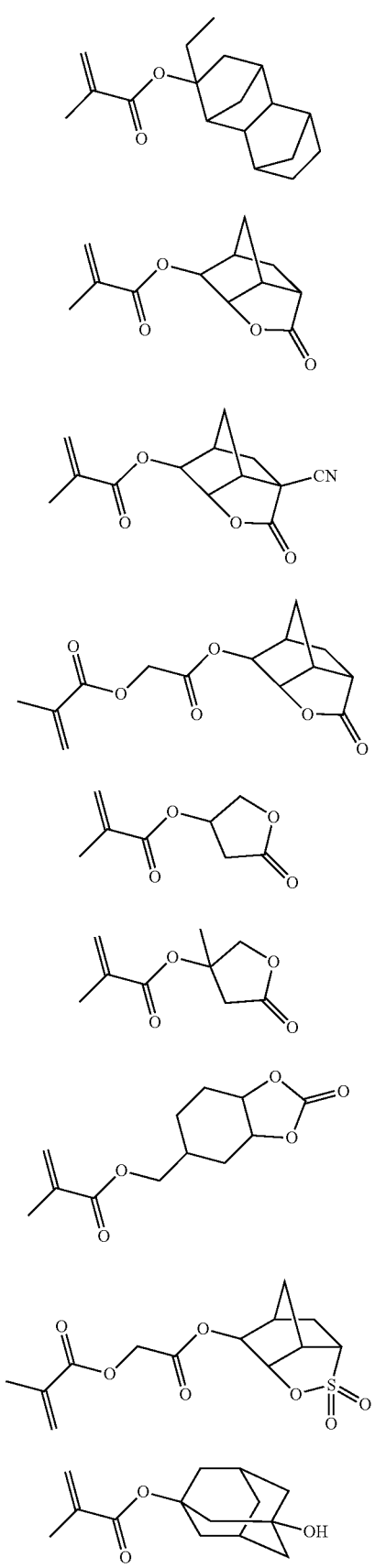

(M-25)

(M-26)

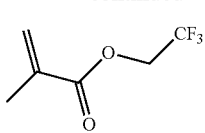

Synthesis of Polymer (A)

Synthesis Example 1

Synthesis of Polymer (A-1)

The compound (M-1), the compound (M-7) and the compound (M-14) as monomers were dissolved in 2-butanone (200 parts by mass) such that the molar ratio became 50/35/15. A monomer solution was prepared by adding to this solution, azobisisobutyronitrile (AIBN) (5 mol %) as a radical polymerization initiator. Into a reaction vessel was placed 2-butanone (100 parts by mass), and purging with nitrogen was conducted for 30 min. The internal temperature of the reaction vessel was adjusted to 80° C., and the monomer solution prepared as described above was added dropwise thereto over 3 hrs with stirring. Onset of the dropwise addition was regarded as the time point of the start of the polymerization reaction, and the polymerization reaction was performed for 6 hrs. After completion of the polymerization reaction, the polymerization reaction liquid was water-cooled to 30° C. or below. The cooled polymerization reaction liquid was charged into methanol (2,000 parts by mass), and thus precipitated white powder was filtered off. The white powder obtained by filtration was washed twice with methanol (400 parts by mass), followed by filtering off, and drying at 60° C. for 15 hrs to give a white powdery polymer (A-1) (yield: 67%). The Mw of the polymer (A-1) was 6,803, and the Mw/Mn was 1.60. Furthermore, as a result of the $^{13}$C-NMR analysis, a ratio of the proportions of a structural unit derived from the compound (M-1): a structural unit derived from the compound (M-7): a structural unit derived from the compound (M-14) was 47: 37: 16 (mol %).

Synthesis Examples 2 to 10

Syntheses of Polymers (A-2) to (A-10)

Polymers (A-2) to (A-10) were obtained by a similar operation to that of Synthesis Example 1 except that each monomer of the type and in the proportion shown in Table 1 below was used. The Mw, the Mw/Mn and the yield (%) of each polymer thus obtained, and the proportion of the structural unit derived from each monomer (mol %) contained in each polymer are shown together in Table 1. In Table 1, "-" indicates that the corresponding monomer was not used.

Synthesis Example 11

Synthesis of Polymer (A-11)

The compound (M-1), the compound (M-13) and the compound (M-18) as monomers were dissolved in 1-methoxy-2-propanol (200 parts by mass) such that the molar ratio became 35/20/45. A monomer solution was prepared by adding to this solution, AIBN (4 mol %) as a radical polymerization initiator. Into a reaction vessel was placed 1-methoxy-2-propanol (100 parts by mass), which was heated to 85° C. with stirring. Next, the monomer solution prepared as described above was added dropwise over 3 hrs and further heated at 85° C. for 3 hrs, and the polymerization reaction was performed for 6 hrs in total. After completion of the polymerization reaction, the polymerization reaction liquid was cooled to room temperature. The cooled polymerization reaction liquid was charged into hexane (500 parts by mass with respect to 100 parts by mass of the polymerization reaction liquid), and thus precipitated white powder was filtered off. The white powder obtained by filtration was washed twice with 100 parts by mass hexane with respect to 100 parts by mass of the polymerization reaction liquid, followed by filtering off and dissolution in 1-methoxy-2-propanol (300 parts by mass). Next, methanol (500 parts by mass), triethylamine (50 parts by mass) and ultra pure water (10 parts by mass) were added to a resulting solution and a hydrolysis reaction was performed at 70° C. for 6 hrs with stirring. After completion of the reaction, the solvent was distilled away and the solid thus obtained was dissolved in acetone (100 parts by mass). A resulting solution was added dropwise into 500 parts by mass of water to permit coagulation of the polymer, and a solid thus obtained was filtered off. Drying at 50° C. for 12 hrs gave a white powdery polymer (A-11) (yield: 68%). The Mw of the polymer (A-11) was 6,711, and the Mw/Mn was 1.34. Furthermore, as a result of the $^{13}$C-NMR analysis, a ratio of the proportions of the structural unit derived from the compound (M-1): a structural unit derived from the compound (M-13): a structural unit derived from the compound (M-18) was 32: 23: 45 (mol %).

Synthesis Examples 12 to 18

Syntheses of Polymers (A-12) to (A-18)

Polymer (A-12) to (A-18) were obtained by a similar operation to that of Synthesis Example 11 except that each monomer of the type and in the proportion shown in Table 1 below was used. The Mw, the Mw/Mn and the yield (%) of each polymer thus obtained, and the proportion of the structural unit derived from each monomer (mol %) contained in each polymer are shown together in Table 1. In Table 1, "-" indicates that the corresponding monomer was not used.

TABLE 1

| (A) Polymer | Monomer that gives structural unit (I) | | | Monomer that gives structural unit (II) | | | Monomer that gives structural unit (III) | | | Monomer that gives other structural unit | | | yield (%) | Mw | Mw/Mn |
|---|---|---|---|---|---|---|---|---|---|---|---|---|---|---|---|
| | type | proportion (mol %) | proportion of structural unit (mol %) | type | proportion (mol %) | proportion of structural unit (mol %) | type | proportion (mol %) | proportion of structural unit (mol %) | type | proportion (mol %) | proportion of structural unit (mol %) | | | |
| Synthesis Example 1 | A-1 | M-1 | 50 | 47 | M-7 | 35 | 37 | — | — | — | M-14 | 15 | 16 | 67 | 6,803 | 1.60 |
| Synthesis Example 2 | A-2 | M-2 | 55 | 52 | M-10/M-12 | 20/25 | 23/25 | — | — | — | — | — | — | 66 | 6,781 | 1.59 |
| Synthesis Example 3 | A-3 | M-3/M-5 | 30/15 | 36/11 | M-13 | 55 | 53 | — | — | — | — | — | — | 65 | 6,9H | 1.68 |
| Synthesis Example 4 | A-4 | M-4/M-6 | 25/25 | 25/23 | M-7 | 50 | 52 | — | — | — | — | — | — | 69 | 7,001 | 1.43 |
| Synthesis Example 5 | A-5 | M-1/M-16 | 20/35 | 19/34 | M-8 | 45 | 47 | — | — | — | — | — | — | 65 | 6,544 | 1.49 |
| Synthesis Example 6 | A-6 | M-2 | 45 | 41 | M-9 | 35 | 39 | — | — | — | M-15 | 20 | 20 | 78 | 6,712 | 1.33 |
| Synthesis Example 7 | A-7 | M-3/M-17 | 30/15 | 27/19 | M-11 | 55 | 54 | — | — | — | — | — | — | 79 | 6,677 | 1.56 |
| Synthesis Example 8 | A-8 | M-2 | 55 | 51 | M-7/M-9 | 30/15 | 31/18 | — | — | — | — | — | — | 74 | 6,681 | 1.55 |
| Synthesis Example 9 | A-9 | M-1 | 30 | 26 | M-10 | 40 | 42 | — | — | — | M-14 | 30 | 32 | 65 | 6,511 | 1.41 |
| Synthesis Example 10 | A-10 | M-1/M-6 | 55/15 | 50/13 | M-13 | 30 | 37 | — | — | — | — | — | — | 66 | 6,433 | 1.38 |
| Synthesis Example 11 | A-11 | M-1 | 35 | 32 | M-13 | 20 | 23 | M-18 | 45 | 45 | — | — | — | 68 | 6,711 | 1.34 |
| Synthesis Example 12 | A-12 | M-2 | 55 | 52 | — | — | — | M-19 | 35 | 40 | M-24 | 10 | 8 | 70 | 6,322 | 1.31 |
| Synthesis Example 13 | A-13 | M-3/M-5 | 25/10 | 23/7 | — | — | — | M-20 | 65 | 70 | — | — | — | 71 | 6,777 | 1.34 |
| Synthesis Example 14 | A-14 | M-1/M-16 | 20/35 | 17/29 | — | — | — | M-23 | 45 | 54 | — | — | — | 65 | 6,533 | 1.35 |
| Synthesis Example 15 | A-15 | M-6/M-17 | 15/55 | 13/55 | — | — | — | M-18 | 30 | 32 | — | — | — | 66 | 6,411 | 1.41 |
| Synthesis Example 16 | A-16 | M-2 | 55 | 52 | — | — | — | M-21 | 45 | 48 | — | — | — | 69 | 6,577 | 1.40 |
| Synthesis Example 17 | A-17 | M-4/M-16 | 25/15 | 24/11 | — | — | — | M-22 | 60 | 65 | — | — | — | 71 | 7,011 | 1.48 |
| Synthesis Example 18 | A-18 | M-6 | 40 | 36 | — | — | — | M-18 | 45 | 46 | M-15 | 15 | 18 | 72 | 6,611 | 1.43 |

Synthesis of Polymer (D)

Synthesis Example 19

Synthesis of Polymer (D-1)

The compounds (M-25) and (M-26) as monomers were dissolved in 2-butanone (200 parts by mass) such that the molar ratio became 50/50. A monomer solution was prepared by adding to this solution, AIBN (5 mol %) as a radical polymerization initiator. Into a reaction vessel was placed 2-butanone (100 parts by mass), and purging with nitrogen was conducted for 30 min. The internal temperature of the reaction vessel was adjusted to 80° C., and the monomer solution prepared as described above was added dropwise thereto over 3 hrs with stirring. Onset of the dropwise addition was regarded as the time point of the start of the polymerization reaction, and the polymerization reaction was performed for 6 hrs. After completion of the polymerization reaction, the polymerization reaction liquid was water-cooled to 30° C. or below. After the solvent was replaced with acetonitrile (400 parts by mass), an operation including: adding hexane (100 parts by mass); stirring the mixture; and collecting the acetonitrile layer was repeated three times. The solvent was replaced with propylene glycol monomethyl ether acetate to give a solution of a polymer (D-1) (yield: 89%). The Mw of the polymer (D-1) was 5,541, and the Mw/Mn was 1.65. Furthermore, as a result of the $^{13}$C-NMR analysis, a ratio of the proportions of a structural unit derived from the compound (M-25): a structural unit derived from the compound (M-26) was 47: 53 (mol %).

Synthesis Example 20

Synthesis of Polymer (D-2)

A polymer (D-2) was obtained by a similar operation to that of Synthesis Example 19 except that each monomer of the type and in the proportion shown in Table 2 below was used. The Mw, the Mw/Mn and the yield (%) of the polymer (D-2), and the proportion of the structural unit derived from each monomer (mol %) contained in the polymer (D-2) are shown together in Table 2.

TABLE 2

| | (D) Polymer | Monomer that gives structural unit (F1) | | | Monomer that gives structural unit (F2) or other structural unit | | | | |
|---|---|---|---|---|---|---|---|---|---|
| | | type | blend proportion (mol %) | proportion of structural unit (mol %) | type | blend proportion (mol %) | proportion of structural unit (mol %) | Yield (%) | Mw | Mw/Mn |
| Synthesis Example 19 | D-1 | M-25 | 50 | 47 | M-26 | 50 | 53 | 89 | 5,541 | 1.65 |
| Synthesis Example 20 | D-2 | M-25 | 70 | 69 | M-14 | 30 | 31 | 81 | 6,033 | 1.70 |

Synthesis of Acid Generating Agent (B)

Compounds (hereinafter, may be also referred to as "acid generating agents (B-1) to (B-13)") represented by the following formulae (B-1) to (B-13) as the acid generating agents (B) used in preparing the radiation-sensitive resin compositions were synthesized in accordance with the following procedure.

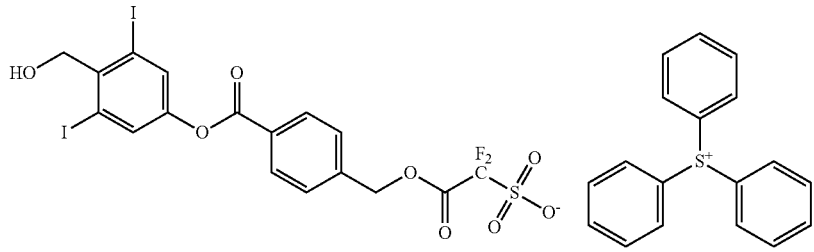

(8-1)

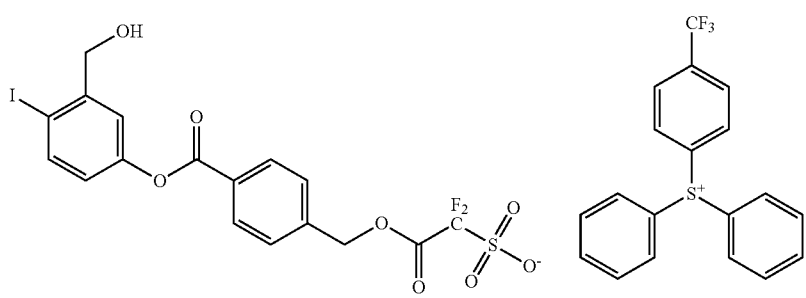

(8-2)

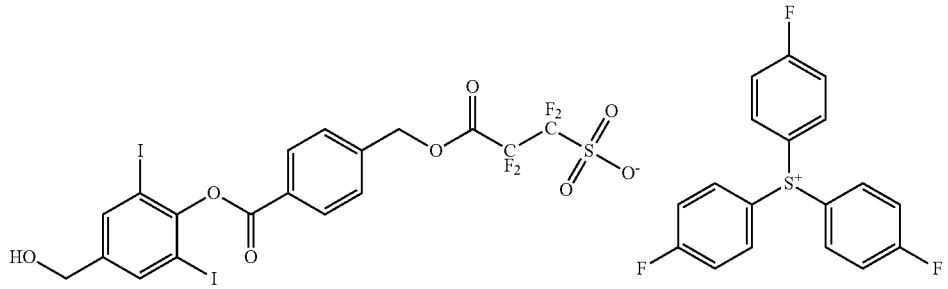

(8-3)

-continued
(8-4)
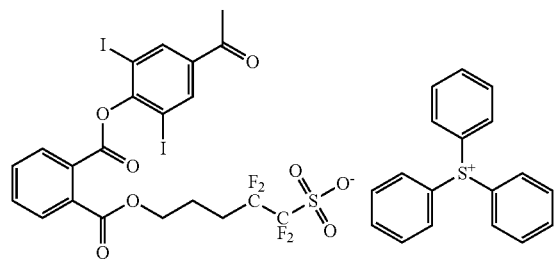
(8-5)
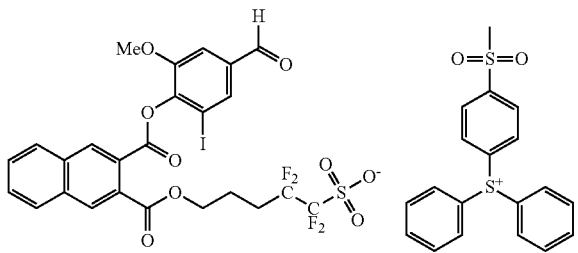
(8-6)
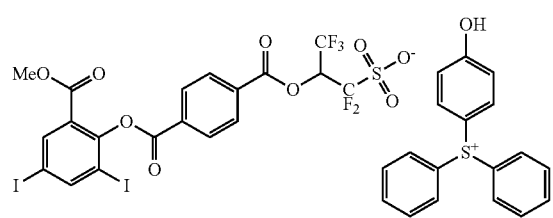
(8-7)
(8-8)
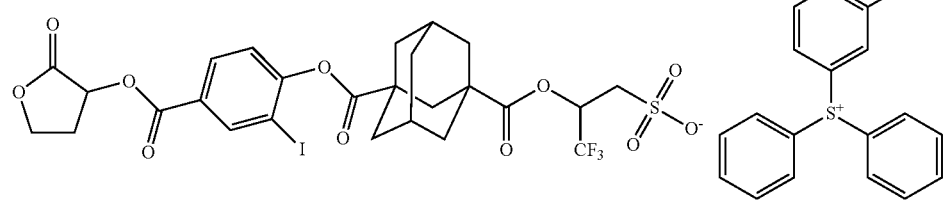
(8-9)
(8-10)
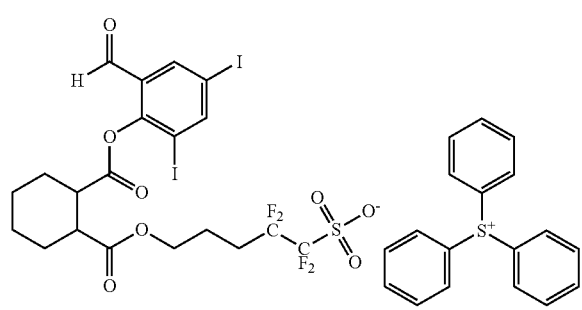
(8-11)
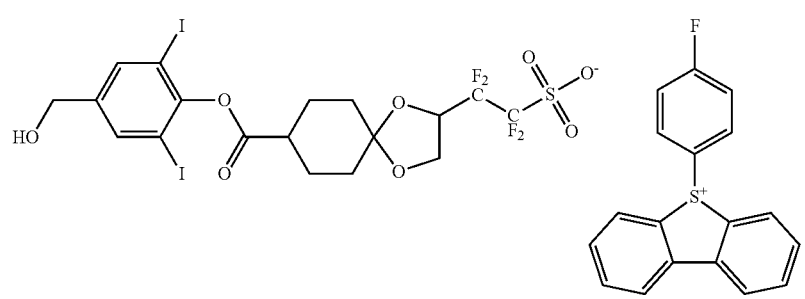
(8-12)
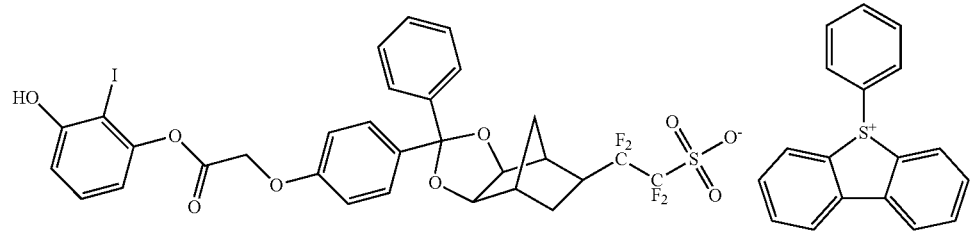

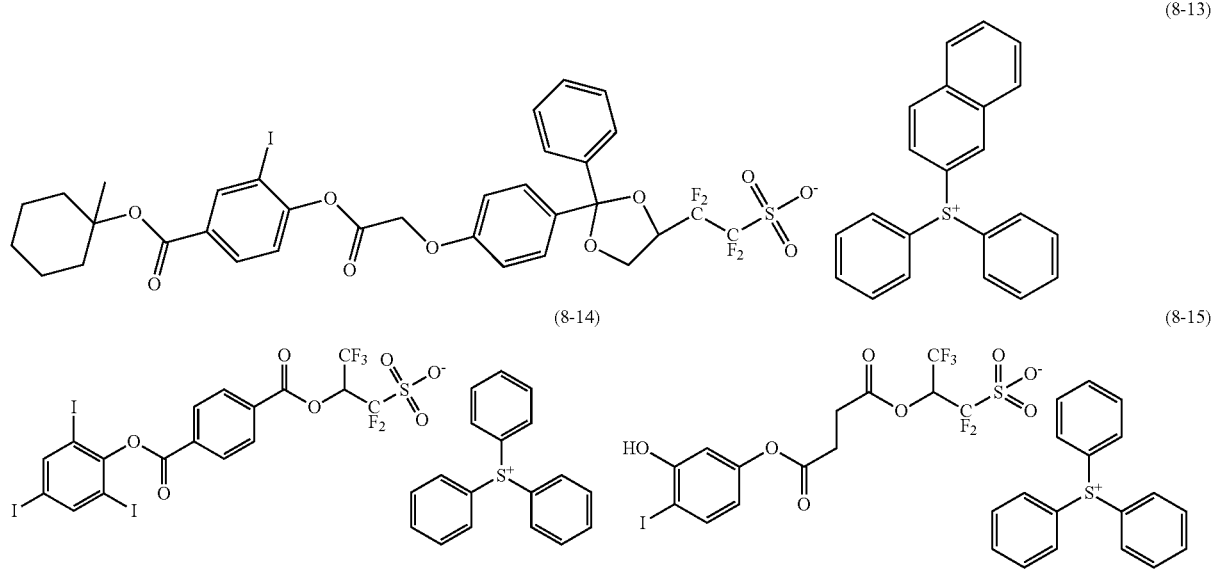

(8-13)

(8-14)

(8-15)

Synthesis Example 21

Synthesis of Acid Generating Agent (B-1)

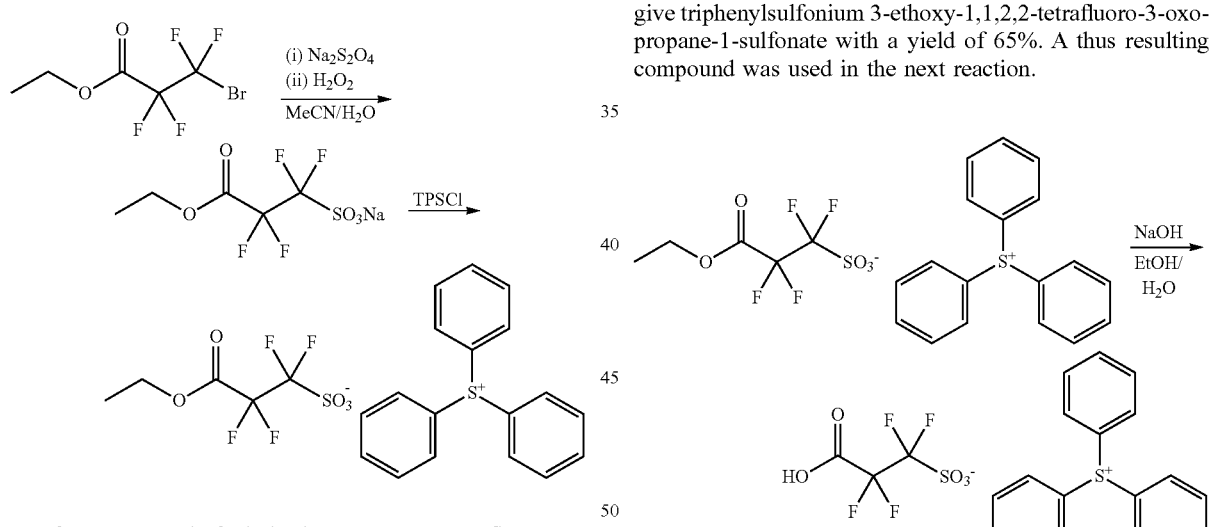

After 59.0 mmol of ethyl 3-bromo-2,2,3,3-tetrafluoropropionate was dissolved in a mixture of acetonitrile: water (1:1 (mass ratio)) to give a 1 M solution, 118.0 mmol of sodium dithionite and 177.0 mmol of sodium bicarbonate were added thereto, and a reaction was allowed at 70° C. for 4 hrs. The reaction product was extracted with acetonitrile and the solvent was distilled away, and then a mixture of acetonitrile: water (3: 1 (mass ratio)) was added thereto to give a 0.5 M solution. To this solution, 109.2 mmol of hydrogen peroxide water and 6.45 mmol of sodium tungstate were added, and the mixture was heated with stirring at 50° C. for 7 hrs. The reaction product was extracted with acetonitrile and the solvent was distilled away to give a sulfonic acid salt compound. To the sulfonic acid salt compound, 59.0 mmol of triphenylsulfonium chloride (TPSCl) was added and a mixture of water: dichloromethane (1: 3 (mass ratio)) was added thereto to give a 0.5 M solution. After the mixture was vigorously stirred at room temperature for 3 hrs, dichloromethane was added to conduct extraction, and the organic layer was separated. The organic layer thus obtained was dried over anhydrous sodium sulfate and the solvent was distilled away, followed by purification with a column to give triphenylsulfonium 3-ethoxy-1,1,2,2-tetrafluoro-3-oxopropane-1-sulfonate with a yield of 65%. A thus resulting compound was used in the next reaction.

In a reaction vessel, after 22.2 mmol of triphenylsulfonium 3-ethoxy-1,1,2,2-tetrafluoro-3-oxopropane-1-sulfonate was dissolved in ethanol to give a 1.0 M solution, the solution was cooled to 0° C. After the cooling, 24.4 mL of a 1.0 M aqueous sodium hydroxide solution was added dropwise and after completion of the dropwise addition, a thus resulting solution was stirred at room temperature for 1 hour. After completion of the reaction, quenching with a saturated aqueous ammonium chloride solution was executed followed by addition of dichloromethane to permit extraction, and the organic layer was separated. After the organic layer thus obtained was dried over anhydrous sodium sulfate, the solvent was distilled away to give triphenylsulfonium 2-carboxy-1,1,2,2-tetrafluoroethane-1- sulfonate with a yield of 55%. A thus resulting compound was used in the next reaction.

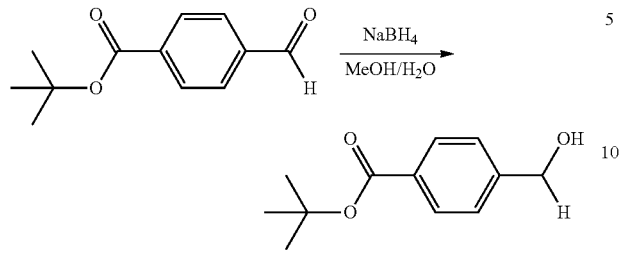

In a reaction vessel, after 20 mmol of tert-butyl 4-formyl benzoate was dissolved in a mixture of methanol: water (1:1 (mass ratio)) to adjust to 1 M, the solution was cooled to 0° C. After the cooling, 22.2 mmol of sodium borohydride was gradually added over 0.5 hrs and then the mixture was stirred at room temperature for 1 hour. After completion of the reaction, quenching with a saturated aqueous ammonium chloride solution was executed followed by addition of ethyl acetate to permit extraction, and the organic layer was separated. After the organic layer thus obtained was dried over anhydrous sodium sulfate, the solvent was eliminated, and purification with a column gave tert-butyl 4-(hydroxymethyl)benzoate with a yield of 91%. A thus resulting compound was used in the next reaction.

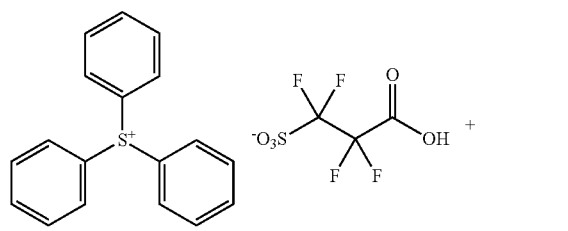

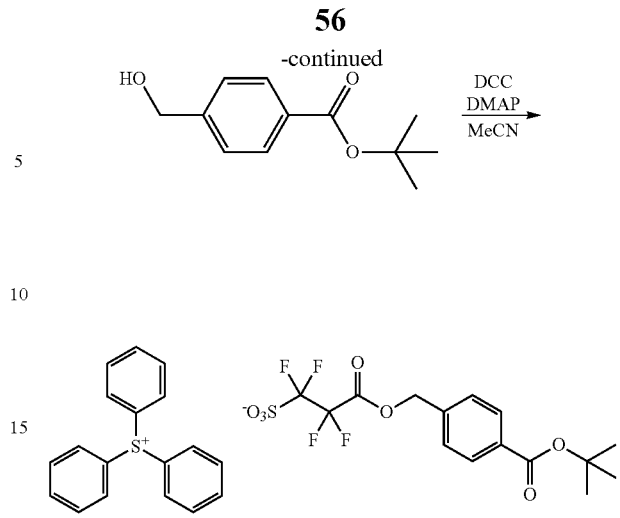

In a reaction vessel, after 10.0 mmol of triphenylsulfonium 2-carboxy-1,1,2,2-tetrafluoroethane-1-sulfonate, 10.5 mmol of tert-butyl 4-(hydroxymethyl)benzoate, and 2 mmol of N,N-dimethyl-4-aminopyridine (DMAP) were dissolved in acetonitrile to give a 1 M solution, the solution was cooled to 0° C. After the cooling, 11 mmol of N,N'-dicyclohexylcarbodiimide (DCC) was gradually added over 0.5 hrs and then the solution was stirred at room temperature for 1 hour. After completion of the reaction, quenching with a saturated aqueous ammonium chloride solution was executed followed by addition of dichloromethane to permit extraction, and the organic layer was separated. After the organic layer thus obtained was dried over anhydrous sodium sulfate, the solvent was eliminated, and purification with a column gave triphenylsulfonium 3-((4-(tert-butoxycarbonyl)benzyl)oxy)-1,1,2,2-tetrafluoro-3-oxopropane-1-sulfonate with a yield of 67%. A thus resulting compound was used in the next reaction.

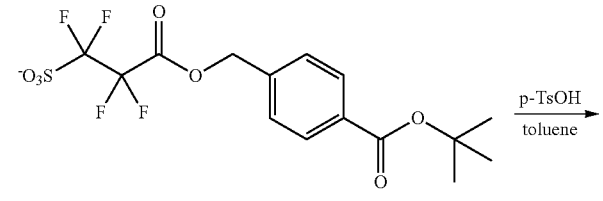

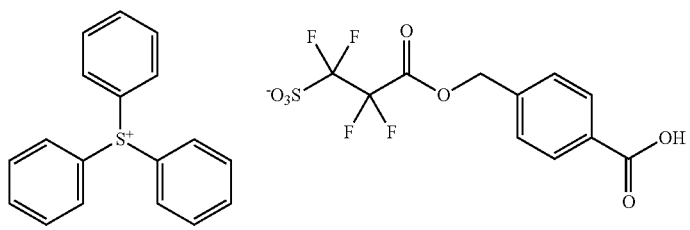

In a reaction vessel, after 6.0 mmol of triphenylsulfonium 3-((4-(tert-butoxycarbonyl)benzyl)oxy)-1,1,2,2-tetrafluoro-3-oxopropane-1-sulfonate, and 3.0 mmol of p-toluenesulfonic acid (p-TsOH) were dissolved in toluene to adjust to 1 M, the solution was stirred for 8 hrs under a reflux condition. After completion of the reaction, quenching with a saturated aqueous sodium bicarbonate solution was executed followed by addition of dichloromethane to permit extraction, and the organic layer was separated. After the organic layer thus obtained was dried over anhydrous sodium sulfate, the solvent was eliminated, and purification with a column gave triphenylsulfonium 3-((4-carboxybenzyl)oxy)-1,1,2,2-tetrafluoro-3-oxopropane-1-sulfonate with a yield of 88%. A thus resulting compound was used in the next reaction.

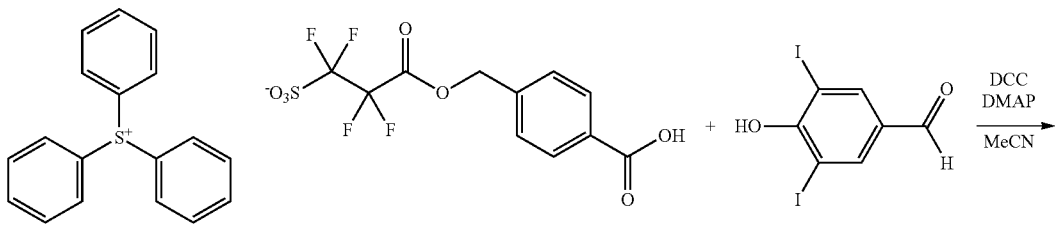

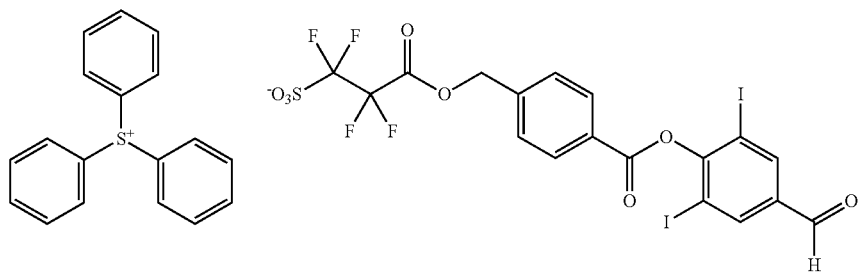

In a reaction vessel, after 5.0 mmol of triphenylsulfonium 3-((4-carboxybenzyl)oxy)-1,1,2,2-tetrafluoro-3-oxopropane-1-sulfonate, 5.5 mmol of 4-hydroxy-3,5-diiodobenzaldehyde, and 1.0 mmol of N,N-dimethyl-4-aminopyridine (DMAP) were dissolved in acetonitrile to adjust to 1 M, the solution was cooled to 0° C. After the cooling, 11 mmol of N,N'-dicyclohexylcarbodiimide (DCC) was gradually added over 0.5 hrs and then the solution was stirred at room temperature for 1 hour. After completion of the reaction, quenching with a saturated aqueous ammonium chloride solution was executed followed by addition of dichloromethane to permit extraction, and the organic layer was separated. After the organic layer thus obtained was dried over anhydrous sodium sulfate, the solvent was eliminated, and purification with a column gave triphenylsulfonium 1,1,2,2-tetrafluoro-3-((4-((4-formyl-2,6-diiodophenoxy)carbonyl)benzyl)oxy)-3-oxopropane-1-sulfonate with a yield of 77%. A thus resulting compound was used in the next reaction.

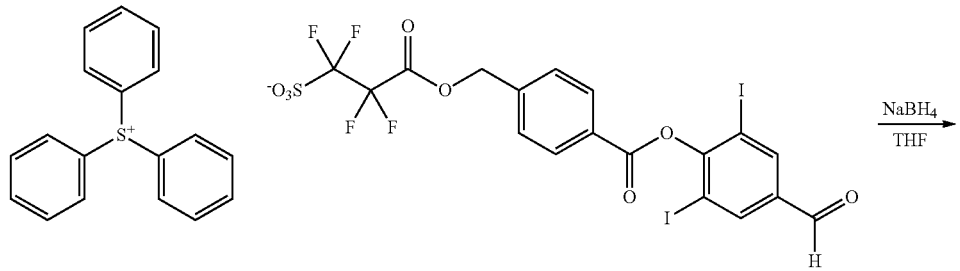

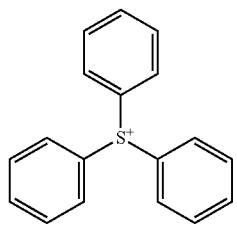 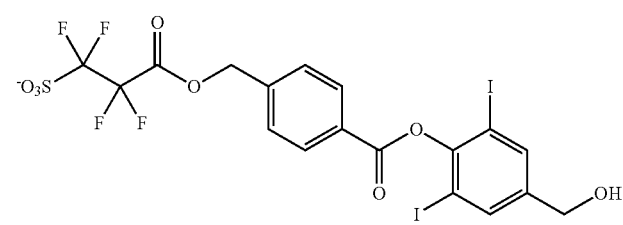

(B-1)

In a reaction vessel, after 4.5 mmol of triphenylsulfonium 1,1,2,2-tetrafluoro-3-((4-((4-formyl-2,6-diiodophenoxy)carbonyl)benzyl)oxy)-3-oxopropane-1-sulfonate was dissolved in tetrahydrofuran to adjust to 1 M, the solution was cooled to 0° C. After the cooling, 5.0 mmol of sodium borohydride was gradually added over 0.5 hrs and then the mixture was stirred at room temperature for 1 hour. After completion of the reaction, quenching with a saturated aqueous ammonium chloride solution was executed followed by addition of dichloromethane to permit extraction, and the organic layer was separated. After the organic layer thus obtained was dried over anhydrous sodium sulfate, the solvent was eliminated, and purification with a column gave an acid generating agent (B-1) with a yield of 91%.

Synthesis Examples 22 and 23

Syntheses of Acid Generating Agents (B-2) and (B-3)

Acid generating agents (B-2) and (B-3) were synthesized in a similar manner to Synthesis Example 21 except that the precursor was appropriately changed.

Synthesis Example 24

Synthesis of Acid Generating Agent (B-4)

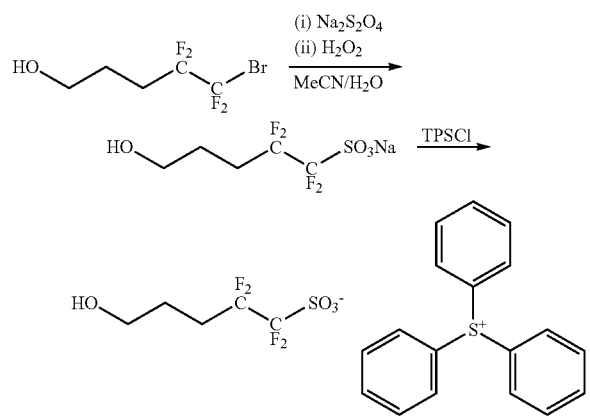

In a reaction vessel, after 59.0 mmol of 5-bromo-4,4,5,5-tetrafluoropentane-1-ol was dissolved in a mixture of acetonitrile: water (1:1 (mass ratio)) to give a 1 M solution, 118.0 mmol of sodium dithionite and 177.0 mmol of sodium bicarbonate were added thereto, and a reaction was allowed at 70° C. for 4 hrs. The reaction product was extracted with acetonitrile and the solvent was distilled away, and then a mixture of acetonitrile: water (3:1 (mass ratio)) was added thereto to give a 0.5 M solution. To this solution, 109.2 mmol of hydrogen peroxide water and 6.45 mmol of sodium tungstate were added, and the mixture was heated with stirring at 50° C. for 7 hrs. The reaction product was extracted with acetonitrile and the solvent was distilled away to give a sulfonic acid salt compound. To the sulfonic acid salt compound, 59.0 mmol of triphenylsulfonium chloride (TPSC1) was added and a mixture of water: dichloromethane (1:3 (mass ratio)) was added thereto to give a 0.5 M solution. After the mixture was vigorously stirred at room temperature for 3 hrs, dichloromethane was added to conduct extraction, and the organic layer was separated. The organic layer thus obtained was dried over anhydrous sodium sulfate and the solvent was distilled away, followed by purification with a column to give triphenylsulfonium 1,1,2,2-tetrafluoro-5-hydroxypentane-1-sulfonate with a yield of 61%. A thus resulting compound was used in the next reaction.

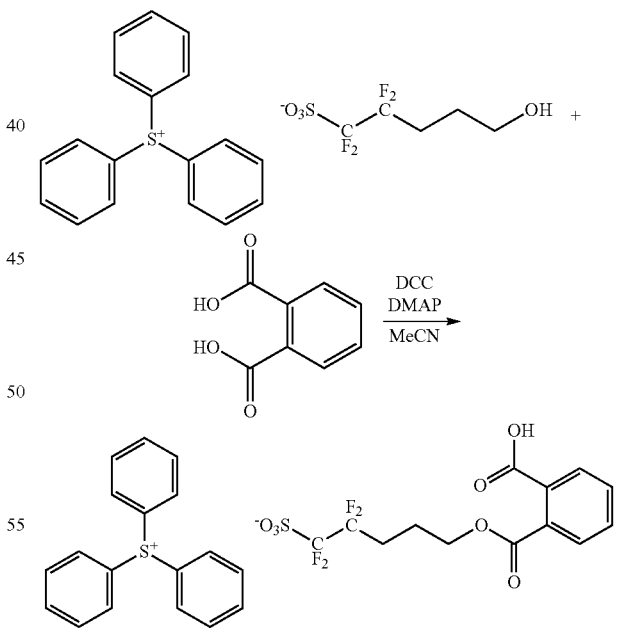

In a reaction vessel, after 30 mmol of triphenylsulfonium 1,1,2,2-tetrafluoro-5-hydroxypentane-1-sulfonate, 30 mmol of phthalic acid, and 3.0 mmol of N,N-dimethyl-4-aminopyridine (DMAP) were dissolved in acetonitrile to give a 1 M solution, the solution was cooled to 0° C. After the cooling, 33 mmol of N,N'-dicyclohexylcarbodiimide (DCC) was gradually added over 0.5 hrs and then the solution was stirred at room temperature for 1 hour. After completion of the reaction, quenching with a saturated aqueous ammonium chloride solution was executed followed by addition of dichloromethane to permit extraction, and the organic layer was separated. After the organic layer thus obtained was dried over anhydrous sodium sulfate, the solvent was eliminated, and purification with a column gave triphenylsulfonium 5-((2-carboxybenzoyl)oxy)-1,1,2,2-tetrafluoropentane-1-sulfonate with a yield of 55%. A thus resulting compound was used in the next reaction.

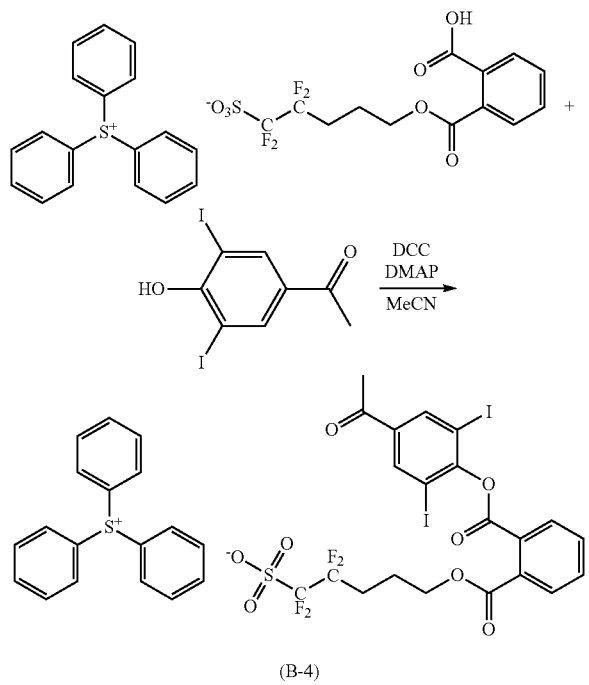

(B-4)

In a reaction vessel, after 15.0 mmol of triphenylsulfonium 5-((2-carboxybenzoyl)oxy)-1,1,2,2-tetrafluoropentane-1-sulfonate, 15.0 mmol of 1-(4-hydroxy-3,5-diiodophenyl)ethan-1-one, and 1.5 mmol of N,N-dimethyl-4-aminopyridine (DMAP) were dissolved in acetonitrile to adjust to 1 M, the solution was cooled to 0° C. After the cooling, 16.5 mmol of N,N'-dicyclohexylcarbodiimide (DCC) was gradually added over 0.5 hrs and then the solution was stirred at room temperature for 1 hour. After completion of the reaction, quenching with a saturated aqueous ammonium chloride solution was executed followed by addition of dichloromethane to permit extraction, and the organic layer was separated. After the organic layer thus obtained was dried over anhydrous sodium sulfate, the solvent was eliminated, and purification with a column gave an acid generating agent (B-4) with a yield of 65%.

Synthesis Examples 25 to 29

Syntheses of Acid Generating Agents (B-5) to (B-9)

Acid generating agents (B-5) to (B-9) were synthesized in a similar manner to Synthesis Example 24 except that the precursor was appropriately changed.

Synthesis Example 30: Synthesis of Acid Generating Agent (B-10)

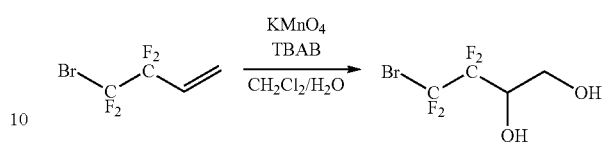

In a reaction vessel, after 50 mmol of 4-bromo-3,3,4,4-tetrafluoro-1-butene and 5 mmol of tetrabutylammonium bromide (TBAB) were dissolved in dichloromethane to adjust to 0.2 M, the solution was cooled to 0° C. After the cooling, 250 mL of a 0.2 M aqueous permanganate potassium solution was added dropwise within a range not leading to temperature elevation exceeding 10° C., and after completion of the dropwise addition, the solution was stirred at room temperature for 24 hrs. After completion of the reaction, the solution was filtered through Celite, and then the organic layer was separated. Dichloromethane was added to a residual aqueous layer to permit extraction, and the resulting solution was added to the organic layer. After the organic layer thus obtained was dried over anhydrous sodium sulfate, the solvent was eliminated, and purification with a column gave 4-bromo-3,3,4,4-tetrafluorobutane-1,2-diol with a yield of 35%. A thus resulting compound was used in the next reaction.

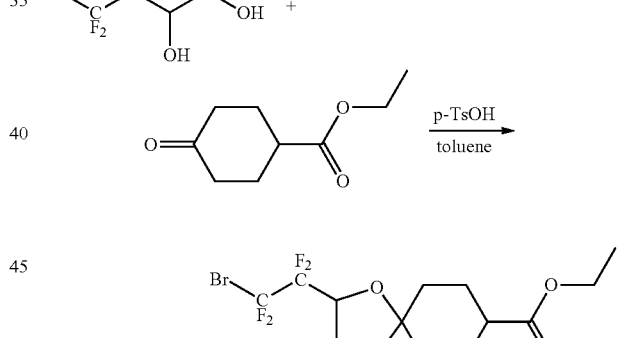

In a reaction vessel, 15 mmol of 4-bromo-3,3,4,4-tetrafluorobutane-1,2-diol, 15 mmol of ethyl 4-oxocyclohexane-1-carboxylate, and 1.5 mmol of p-toluenesulfonic acid (p-TsOH) were dissolved in toluene to adjust to 1 M. A Dean-Stark apparatus was attached to the reaction vessel, and the solution was stirred for 1 hour under a reflux condition. After completion of the reaction, quenching with a saturated aqueous sodium bicarbonate solution was executed followed by addition of ethyl acetate to permit extraction, and the organic layer was separated. After the organic layer thus obtained was dried over anhydrous sodium sulfate, the solvent was eliminated, and purification with a column gave ethyl 2-(2-bromo-1,1,2,2-tetrafluoroethyl)-1,4-dioxaspiro[4.5]decane-8-carboxylate with a yield of 95%. A thus resulting compound was used in the next reaction.

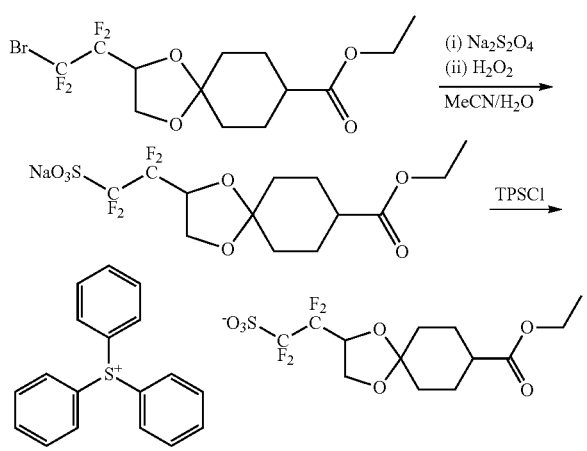

In a reaction vessel, after 14.0 mmol of ethyl 2-(2-bromo-1,1,2,2-tetrafluoroethyl)-1,4-dioxaspiro[4.5]decane-8-carboxylate was dissolved in a mixture of acetonitrile: water (1:1 (mass ratio)) to give a 1 M solution, 28.0 mmol of sodium dithionite and 40.6 mmol of sodium bicarbonate were added thereto, and a reaction was allowed at 70° C. for 4 hrs. The reaction product was extracted with acetonitrile and the solvent was distilled away, and then a mixture of acetonitrile: water (3: 1 (mass ratio)) was added thereto to give a 0.5 M solution. To this solution, 24.5 mmol of hydrogen peroxide water and 1.54 mmol of sodium tungstate were added, and the mixture was heated with stirring at 50° C. for 7 hrs. The reaction product was extracted with acetonitrile and the solvent was distilled away to give a sulfonic acid salt compound. To the sulfonic acid salt compound, 14.0 mmol of triphenylsulfonium chloride (TPSC1) was added and a mixture of water: dichloromethane (1: 3 (mass ratio)) was added thereto to give a 0.5 M solution. After the mixture was vigorously stirred at room temperature for 3 hrs, dichloromethane was added to conduct extraction, and the organic layer was separated. The organic layer thus obtained was dried over anhydrous sodium sulfate and the solvent was distilled away, followed by purification with a column to give triphenylsulfonium 2-(8-(ethoxycarbonyl)-1,4-dioxaspiro[4.5]decan-2-yl)-1,1,2,2-tetrafluoroethane-1-sulfonate with a yield of 67%. A thus resulting compound was used in the next reaction.

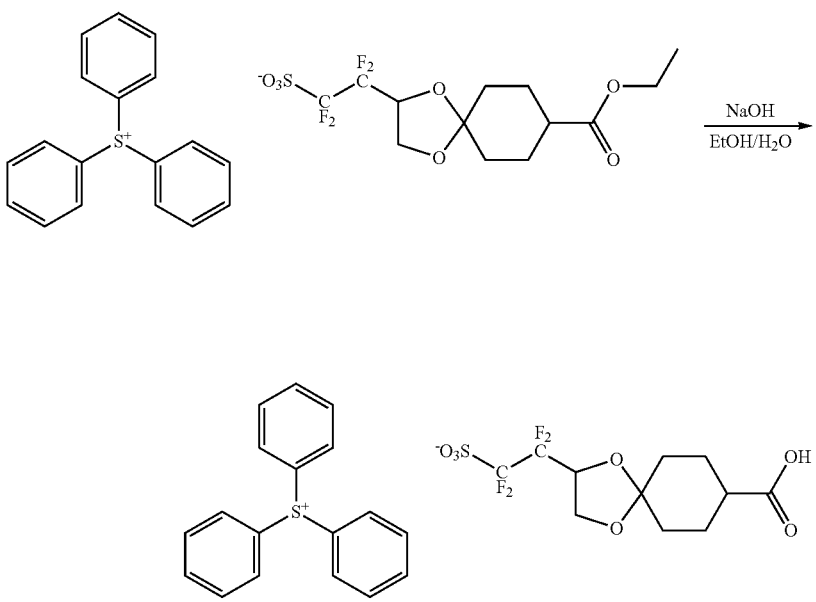

In a reaction vessel, after 8.0 mmol of triphenylsulfonium 2-(8-(ethoxycarbonyl)-1,4-dioxaspiro[4.5]decan-2-yl)-1,1,2,2-tetrafluoroethane-1-sulfonate was dissolved in ethanol to adjust to 1 M, the solution was cooled to 0° C. After the cooling, 8 mL of a 1 M aqueous sodium hydroxide solution was added dropwise within a range not leading to temperature elevation exceeding 10° C., and after completion of the dropwise addition, the mixture was stirred at room temperature for 1 hour. After completion of the reaction, quenching with 2 M hydrochloric acid was executed followed by addition of dichloromethane to permit extraction, and the organic layer was separated. The organic layer thus obtained was dried over anhydrous sodium sulfate and the solvent was distilled away. Thereafter, purification with a column gave triphenylsulfonium 2-(8-carboxy-1,4-dioxaspiro[4.5]decan-2-yl)-1,1,2,2-tetrafluoroethane-1-sulfonate with a yield of 95%. A thus resulting compound was used in the next reaction.

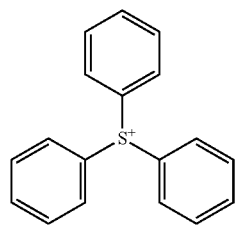 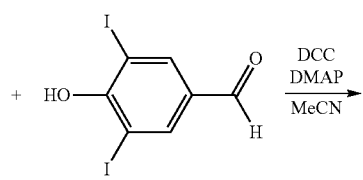

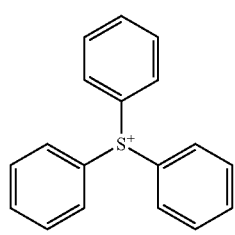 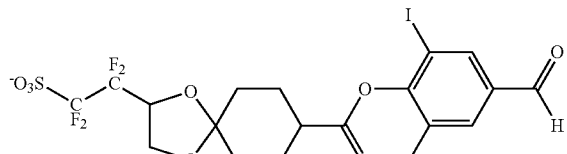

(B-10)

In a reaction vessel, after 7.5 mmol of triphenylsulfonium 2-(8-carboxy-1,4-dioxaspiro[4.5]decan-2-yl)-1,1,2,2-tetrafluoroethane-1-sulfonate, 8.0 mmol of 4-hydroxy-3,5-diiodobenzaldehyde, and 1.5 mmol of N,N-dimethyl-4-aminopyridine (DMAP) were dissolved in acetonitrile to adjust to 1 M, the solution was cooled to 0° C. After the cooling, 16.5 mmol of N,N'-dicyclohexylcarbodiimide (DCC) was gradually added over 0.5 hrs and then the solution was stirred at room temperature for 1 hour. After completion of the reaction, quenching with a saturated aqueous ammonium chloride solution was executed followed by addition of dichloromethane to permit extraction, and the organic layer was separated. After the organic layer thus obtained was dried over anhydrous sodium sulfate, the solvent was eliminated, and purification with a column gave an acid generating agent (B-10) with a yield of 79%.

Synthesis Examples 31 to 33

Syntheses of Acid Generating Agents (B-11) to (B-13)

Acid generating agents (B-11) to (B-13) were synthesized in a similar manner to Synthesis Example 30 except that the precursor was appropriately changed.

Preparation of Radiation-Sensitive Resin Composition

The acid generating agent (B), the acid diffusion control agent (C) and the solvent (E) used for preparing the radiation-sensitive resin compositions are shown below.

(B) Acid Generating Agent

Examples: acid generating agents (B-1) to (B-13) synthesized as described above Comparative Examples: compounds represented by the above formulae (B-14) and (B-15)

(C) Acid Diffusion Control Agent

C-1 to C-6: compounds represented by the following formulae (C-1) to (C-6)

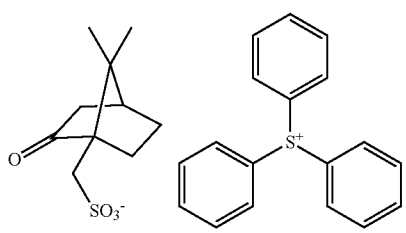

(C-1)

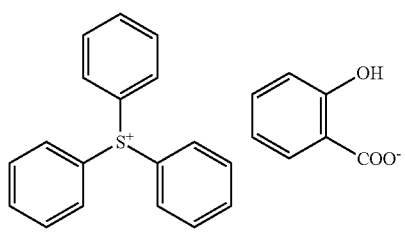

(C-2)

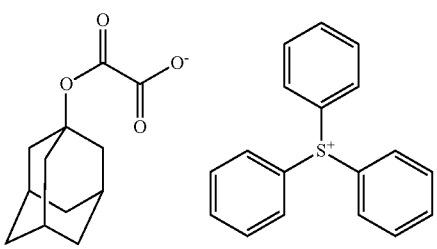

(C-3)

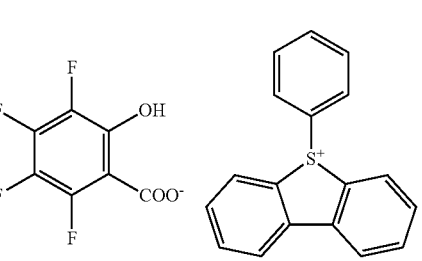

(C-4)

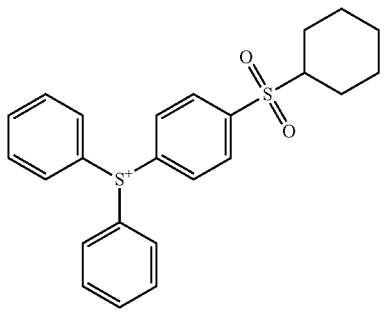

(C-5)

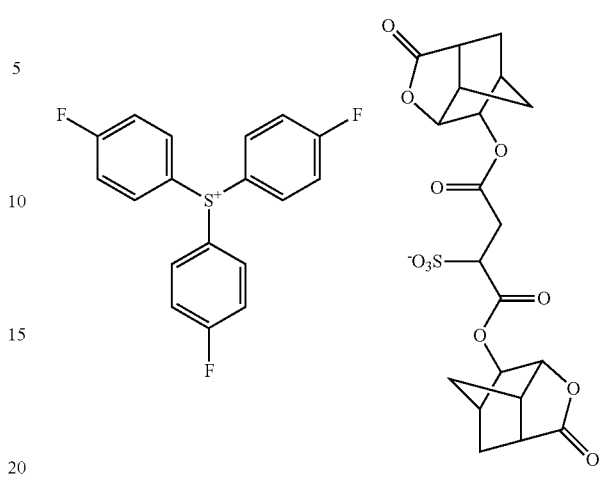

(C-6)

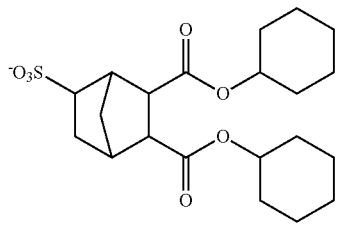

(E) Solvent
 E-1: propylene glycol monomethyl ether acetate
 E-2: propylene glycol monomethyl ether Example 1

A radiation-sensitive resin composition (J-1) was prepared by: mixing 100 parts by mass of (A-1) as the polymer (A), 15 parts by mass of (B-1) as the acid generating agent (B), 4.5 parts by mass of (C-2) as the acid diffusion control agent (C), 7 parts by mass of (D-2) as the polymer (D), and as the solvent (E), 4,280 parts by mass of (E-1) and 1,830 parts by mass of (E-2); and filtering a resulting mixture through a membrane filter having a pore size of 0.2 μm.

Examples 2 to 30, and Comparative Examples 1 and 2

Radiation-sensitive resin compositions (J-2) to (J-30), and (CJ-1) and (CJ-2) were prepared in a similar manner to Example 1 except that for each component, the type and content shown in Table 3 below were used.

TABLE 3

| | Radiation-sensitive resin composition | (A) Polymer type | content (parts by mass) | (B) Acid generating agent type | content (parts by mass) | (C) Acid diffusion control agent type | content (parts by mass) | (D) Polymer type | content (parts by mass) | (E) Solvent type | content (parts by mass) |
|---|---|---|---|---|---|---|---|---|---|---|---|
| Example 1 | J-1 | A-1 | 100 | B-1 | 15 | C-2 | 4.5 | D-2 | 7 | E-1/E-2 | 4,280/1,830 |
| Example 2 | J-2 | A-1 | 100 | B-2 | 25 | C-2 | 7.5 | D-2 | 7 | E-1/E-2 | 4,280/1,830 |
| Example 3 | J-3 | A-1 | 100 | B-3 | 20 | C-2 | 6 | D-2 | 7 | E-1/E-2 | 4,280/1,830 |
| Example 4 | J-4 | A-1 | 100 | B-4 | 15 | C-2 | 4.5 | D-2 | 7 | E-1/E-2 | 4,280/1,830 |
| Example 5 | J-5 | A-1 | 100 | B-5 | 15 | C-2 | 4.5 | D-2 | 7 | E-1/E-2 | 4,280/1,830 |
| Example 6 | J-6 | A-1 | 100 | B-6 | 30 | C-2 | 9 | D-2 | 7 | E-1/E-2 | 4,280/1,830 |
| Example 7 | J-7 | A-1 | 100 | B-7 | 20 | C-2 | 6 | D-2 | 7 | E-1/E-2 | 4,280/1,830 |
| Example 8 | J-8 | A-1 | 100 | B-8 | 15 | C-2 | 4.5 | D-2 | 7 | E-1/E-2 | 4,280/1,830 |
| Example 9 | J-9 | A-1 | 100 | B-9 | 10 | C-2 | 3 | D-2 | 7 | E-1/E-2 | 4,280/1,830 |
| Example 10 | J-10 | A-1 | 100 | B-10 | 20 | C-2 | 6 | D-2 | 7 | E-1/E-2 | 4,280/1,830 |
| Example 11 | J-11 | A-1 | 100 | B-11 | 15 | C-2 | 4.5 | D-2 | 7 | E-1/E-2 | 4,280/1,830 |
| Example 12 | J-12 | A-1 | 100 | B-12 | 25 | C-2 | 7.5 | D-2 | 7 | E-1/E-2 | 4,280/1,830 |
| Example 13 | J-13 | A-1 | 100 | B-13 | 20 | C-2 | 6 | D-2 | 7 | E-1/E-2 | 4,280/1,830 |
| Example 14 | J-14 | A-2 | 100 | B-1 | 15 | C-1 | 4.5 | D-2 | 7 | E-1/E-2 | 4,280/1,830 |
| Example 15 | J-15 | A-3 | 100 | B-9 | 10 | C-3 | 3 | D-2 | 7 | E-1/E-2 | 4,280/1,830 |
| Example 16 | J-16 | A-4 | 100 | B-12 | 25 | C-5 | 7.5 | D-2 | 7 | E-1/E-2 | 4,280/1,830 |
| Example 17 | J-17 | A-5 | 100 | B-11 | 15 | C-6 | 4.5 | D-2 | 7 | E-1/E-2 | 4,280/1,830 |
| Example 18 | J-18 | A-6 | 100 | B-4 | 15 | C-1 | 4.5 | D-2 | 7 | E-1/E-2 | 4,280/1,830 |
| Example 19 | J-19 | A-7 | 100 | B-9 | 10 | C-2 | 3 | D-2 | 7 | E-1/E-2 | 4,280/1,830 |

TABLE 3-continued

| | | (A) Polymer | | (B) Acid generating agent | | (C) Acid diffusion control agent | | (D) Polymer | | (E) Solvent | |
|---|---|---|---|---|---|---|---|---|---|---|---|
| | Radiation-sensitive resin composition | type | content (parts by mass) | type | content (parts by mass) | type | content (parts by mass) | type | content (parts by mass) | type | content (parts by mass) |
| Example 20 | J-20 | A-8 | 100 | B-2 | 25 | C-3 | 7.5 | D-2 | 7 | E-1/E-2 | 4,280/1,830 |
| Example 21 | J-21 | A-9 | 100 | B-3 | 20 | C-4 | 6 | D-2 | 7 | E-1/E-2 | 4,280/1,830 |
| Example 22 | J-22 | A-10 | 100 | B-5 | 15 | C-2 | 4.5 | D-2 | 7 | E-1/E-2 | 4,280/1,830 |
| Example 23 | J-23 | A-11 | 100 | B-10 | 20 | C-2 | 6 | D-1 | 7 | E-1/E-2 | 4,280/1,830 |
| Example 24 | J-24 | A-12 | 100 | B-8 | 15 | C-2 | 4.5 | D-1 | 7 | E-1/E-2 | 4,280/1,830 |
| Example 25 | J-25 | A-13 | 100 | B-7 | 20 | C-1 | 6 | D-1 | 7 | E-1/E-2 | 4,280/1,830 |
| Example 26 | J-26 | A-14 | 100 | B-6 | 30 | C-5 | 9 | D-1 | 7 | E-1/E-2 | 4,280/1,830 |
| Example 27 | J-27 | A-15 | 100 | B-13 | 20 | C-3 | 6 | D-1 | 7 | E-1/E-2 | 4,280/1,830 |
| Example 28 | J-28 | A-16 | 100 | B-1 | 15 | C-1 | 4.5 | D-1 | 7 | E-1/E-2 | 4,280/1,830 |
| Example 29 | J-29 | A-17 | 100 | B-1 | 15 | C-3 | 4.5 | D-1 | 7 | E-1/E-2 | 4,280/1,830 |
| Example 30 | J-30 | A-18 | 100 | B-3 | 20 | C-4 | 6 | D-1 | 7 | E-1/E-2 | 4,280/1,830 |
| Comparative Example 1 | CJ-1 | A-1 | 100 | B-14 | 15 | C-2 | 4.5 | D-2 | 7 | E-1/E-2 | 4,280/1,830 |
| Comparative Example 2 | CJ-2 | A-1 | 100 | B-15 | 15 | C-2 | 4.5 | D-2 | 7 | E-1/E-2 | 4,280/1,830 |

Resist Pattern Formation

An underlayer antireflective film having an average thickness of 105 nm was formed by applying a composition for underlayer antireflective film formation ("ARC66" available from Brewer Science, Inc.) on the surface of a 12-inch silicon wafer using a spin-coater ("CLEAN TRACK ACT12" available from Tokyo Electron Limited), and thereafter baking the composition at 205° C. for 60 sec. Each radiation-sensitive resin composition prepared as described above was applied on the underlayer antireflective film using the spin-coater, and subjected to PB at 130° C. for 60 sec. Thereafter, by cooling at 23° C. for 30 sec, a resist film having an average thickness of 55 nm was formed. Next, the resist film was exposed using an EUV scanner ("NXE3300", available from ASML Co.,) with NA of 0.33 under an illumination condition involving Conventional s=0.89 and with a mask of imecDEFECT32FFR02. After the exposure, PEB was carried out at 120° C. for 60 sec. Thereafter, the resist film was developed with an alkali by using a 2.38% by mass aqueous TMAH solution as an alkaline developer solution, followed by washing with water and further drying to form a positive-tone resist pattern (32-nm line-and-space pattern).

Evaluations

The radiation-sensitive resin compositions prepared as described above were evaluated on sensitivity, a depth of focus and an exposure latitude in accordance with the following method. The results of the evaluations are shown in Table 4 below. It is to be noted that a scanning electron microscope ("CG-5000" available from Hitachi High-Technologies Corporation) was used for line-width measurement of the resist pattern.

Sensitivity

An exposure dose at which a 32-nm line-and-space pattern was formed in the aforementioned resist pattern formation was defined as an optimum exposure dose (Eop), and this optimum exposure dose was adopted as sensitivity (mJ/cm$^2$). The sensitivity may be evaluated to be: "favorable" in a case of being no greater than 40 mJ/cm$^2$; and "unfavorable" in a case of exceeding 40 mJ/cm$^2$.

Depth of Focus

On the resist pattern which was resolved at the optimum exposure dose, the dimension of a pattern formed when the focus was shifted along the depth direction was observed, a latitude in the depth direction in which the pattern dimension falls within the range of 90% to 110% of the basis without being accompanied by a bridge and/or residue was determined, and the measurement was defined as "depth of focus (nm)". The depth of focus may be evaluated to be: "favorable" in a case of exceeding 50 nm; and "unfavorable" in a case of being no greater than 50 nm.

Exposure Latitude

An exposure dose was altered stepwise by 1 mJ/cm$^2$ within an exposure dose range including the optimum exposure dose, and a resist pattern was formed at each exposure dose. The line width of each resist pattern was measured using the scanning electron microscope. An exposure dose E (40) at which the line width of 40 nm was attained and an exposure dose E (20) at which the line width of 20 nm was attained were determined from the relationship between the line width obtained and the exposure dose, and the exposure latitude (%) was calculated using the following equation: exposure latitude=[E(40)–E(20)]×100/(optimum exposure dose). The "exposure latitude" value being greater indicates less variation of the dimension of the formed pattern with a variation of the exposure dose, leading to a higher process yield in the production of devices. The exposure latitude may be evaluated to be: "favorable" in a case of being no less than 20%; and "unfavorable" in a case of being less than 20%.

TABLE 4

| | Radiation-sensitive resin composition | Sensitivity (mJ/cm$^2$) | Depth of focus (nm) | Exposure latitude (%) |
|---|---|---|---|---|
| Example 1 | J-1 | 29 | 80 | 32 |
| Example 2 | J-2 | 25 | 80 | 32 |
| Example 3 | J-3 | 27 | 90 | 36 |
| Example 4 | J-4 | 38 | 60 | 24 |
| Example 5 | J-5 | 35 | 60 | 24 |
| Example 6 | J-6 | 37 | 70 | 28 |
| Example 7 | J-7 | 30 | 80 | 32 |
| Example 8 | J-8 | 27 | 70 | 28 |
| Example 9 | J-9 | 36 | 70 | 28 |
| Example 10 | J-10 | 34 | 60 | 24 |
| Example 11 | J-11 | 28 | 90 | 36 |
| Example 12 | J-12 | 24 | 80 | 32 |

TABLE 4-continued

| | Radiation-sensitive resin composition | Sensitivity (mJ/cm²) | Depth of focus (nm) | Exposure latitude (%) |
|---|---|---|---|---|
| Example 13 | J-13 | 30 | 70 | 28 |
| Example 14 | J-14 | 28 | 80 | 32 |
| Example 15 | J-15 | 35 | 70 | 28 |
| Example 16 | J-16 | 25 | 80 | 32 |
| Example 17 | J-17 | 27 | 90 | 36 |
| Example 18 | J-18 | 37 | 60 | 24 |
| Example 19 | J-19 | 35 | 70 | 28 |
| Example 20 | J-20 | 27 | 80 | 32 |
| Example 21 | J-21 | 28 | 80 | 32 |
| Example 22 | J-22 | 34 | 60 | 24 |
| Example 23 | J-23 | 32 | 60 | 24 |
| Example 24 | J-24 | 28 | 70 | 28 |
| Example 25 | J-25 | 31 | 80 | 32 |
| Example 26 | J-26 | 39 | 70 | 28 |
| Example 27 | J-27 | 31 | 70 | 28 |
| Example 28 | J-28 | 28 | 80 | 32 |
| Example 29 | J-29 | 27 | 80 | 32 |
| Example 30 | J-30 | 26 | 80 | 32 |
| Comparative Example 1 | CJ-1 | 50 | 30 | 12 |
| Comparative Example 2 | CJ-2 | 26 | 40 | 16 |

As is clear from the results shown in Table 4, the radiation-sensitive resin compositions of Examples were superior in the sensitivity, depth of focus, and exposure latitude.

According to the radiation-sensitive resin composition and the resist pattern-forming method of the embodiments of the present invention, a resist pattern can be formed with a sensitivity, a depth of focus and an exposure latitude each being superior. The radiation-sensitive acid generating agent of the embodiment of the present invention can be suitably used as a radiation-sensitive acid generating component of the radiation-sensitive resin composition. The compound of the embodiment of the present invention can be suitably used as a source material of the radiation-sensitive acid generating agent. Therefore, these can be suitably used for working processes of semiconductor devices, and the like, in which microfabrication is expected to be further in progress hereafter.

Obviously, numerous modifications and variations of the present invention are possible in light of the above teachings. It is therefore to be understood that within the scope of the appended claims, the invention may be practiced otherwise than as specifically described herein.

What is claimed is:

1. A radiation-sensitive resin composition comprising:
a polymer that comprises a structural unit comprising an acid-labile group; and
a radiation-sensitive acid generating agent,
wherein the radiation-sensitive acid generating agent is a compound represented by formula (1):

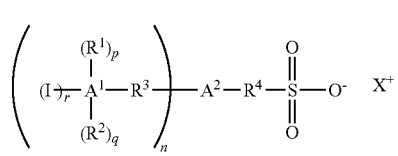

(1)

wherein, in the formula (1),
A¹ represents a group obtained from a compound which comprises a ring having 3 to 20 ring atoms by removing (p+q+r+1) hydrogen atoms on the ring;
R¹ represents a monovalent group having 0 to 10 carbon atoms which comprises at least one of an oxygen atom and a nitrogen atom;
R² represents a monovalent hydrocarbon group having 1 to 20 carbon atoms, a monovalent halogenated hydrocarbon group having 1 to 20 carbon atoms or a halogen atom;
p is an integer of 1 to 10, q is an integer of 0 to 9 and r is an integer of 1 to 10, wherein (p+q+r) is no greater than 11;
R³ represents a single bond, —O— or —COO—;
A² represents an organic group having a valency of (n+1) and having 3 to 30 carbon atoms that comprises a ring having 3 to 20 ring atoms;
n is an integer of 1 to 3, wherein
in a case in which there exist a plurality of R¹s, the plurality of R¹s are identical or different from each other,
in a case in which there exist a plurality of R²s, the plurality of R²s are identical or different from each other, and
in a case in which n is no less than 2, a plurality of A¹s are identical or different from each other, a plurality of R³s are identical or different from each other, a plurality of p's are identical or different from each other, a plurality of q's are identical or different from each other, and a plurality of r's are identical or different from each other;
R⁴ represents a fluorinated alkanediyl group having 1 to 10 carbon atoms; and
X⁺ represents a monovalent radiation-sensitive onium cation.

2. The radiation-sensitive resin composition according to claim 1, wherein the ring comprised in A¹ in the formula (1) is an aromatic ring having 6 to 20 ring atoms.

3. The radiation-sensitive resin composition according to claim 1, wherein R⁴ in the formula (1) is represented by formula (F):

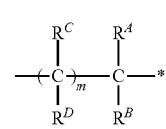

(F)

wherein, in the formula (F),
R$^A$ and R$^B$ each independently represent a hydrogen atom or a fluorine atom;
R$^C$ and R$^D$ each independently represent a hydrogen atom, a fluorine atom or a perfluoroalkyl group having 1 to 10 carbon atoms;
m is an integer of 0 to 3, wherein
in a case in which m is no less than 2, a plurality of R$^C$s are identical or different from each other, a plurality of R$^D$s are identical or different from each other, and at least one of R$^A$, R$^B$, one or a plurality of R$^C$s and one or a plurality of R$^D$s represents a fluorine atom or a perfluoroalkyl group; and
* denotes a site that bonds to a sulfur atom of —S(=O)₂—O⁻ in the formula (1).

4. The radiation-sensitive resin composition according to claim 1, wherein $R^1$ in the formula (1) represents a hydroxy group, a hydroxyhydrocarbon group, a group comprising a lactone structure, an acyl group or a carbonyloxyhydrocarbon group.

5. The radiation-sensitive resin composition according to claim 1, wherein the ring in $A^2$ in the formula (1) is an aromatic ring, an aliphatic ring, an aliphatic heterocyclic ring, an aromatic ring and an aliphatic ring, an aromatic ring and an aliphatic heterocyclic ring, or an aliphatic ring and an aliphatic heterocyclic ring.

6. The radiation-sensitive resin composition according to claim 1, wherein the ring comprised in $A^1$ in the formula (1) is an aromatic ring.

7. A resist pattern-forming method comprising:
applying a radiation-sensitive resin composition directly or indirectly on a substrate to form a resist film;
exposing the resist film; and
developing the resist film exposed,
wherein the radiation-sensitive resin composition comprises:
a polymer that comprises a structural unit comprising an acid-labile group; and
a radiation-sensitive acid generating agent,
wherein the radiation-sensitive acid generating agent is a compound represented by formula (1):

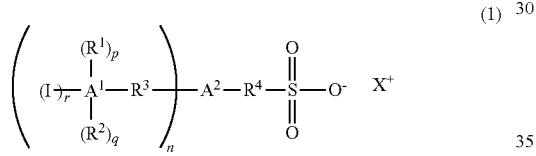

wherein, in the formula (1),
$A^1$ represents a group obtained from a compound which comprises a ring having 3 to 20 ring atoms by removing (p+q+r+1) hydrogen atoms on the ring;
$R^1$ represents a monovalent group having 0 to 10 carbon atoms which comprises at least one of an oxygen atom and a nitrogen atom;
$R^2$ represents a monovalent hydrocarbon group having 1 to 20 carbon atoms, a monovalent halogenated hydrocarbon group having 1 to 20 carbon atoms or a halogen atom;
p is an integer of 1 to 10, q is an integer of 0 to 9 and r is an integer of 1 to 10, wherein (p+q+r) is no greater than 11;
$R^3$ represents a single bond, —O— or —COO—;
$A^2$ represents an organic group having a valency of (n+1) and having 3 to 30 carbon atoms that comprises a ring having 3 to 20 ring atoms;
n is an integer of 1 to 3, wherein
in a case in which there exist a plurality of $R^1$s, the plurality of $R^1$s are identical or different from each other,
in a case in which there exist a plurality of $R^2$s, the plurality of $R^2$s are identical or different from each other, and
in a case in which n is no less than 2, a plurality of $A^1$s are identical or different from each other, a plurality of $R^3$s are identical or different from each other, a plurality of p's are identical or different from each other, a plurality of p's are identical or different from each other, and a plurality of r's are identical or different from each other;
$R^4$ represents a fluorinated alkanediyl group having 1 to 10 carbon atoms; and
$X^+$ represents a monovalent radiation-sensitive onium cation.

8. The resist pattern-forming method according to claim 7, wherein the ring comprised in $A^1$ in the formula (1) is an aromatic ring having 6 to 20 ring atoms.

9. The resist pattern-forming method according to claim 7, wherein $R^4$ in the formula (1) is represented by formula (F):

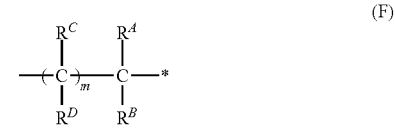

wherein, in the formula (F),
$R^A$ and $R^B$ each independently represent a hydrogen atom or a fluorine atom;
$R^C$ and $R^D$ each independently represent a hydrogen atom, a fluorine atom or a perfluoroalkyl group having 1 to 10 carbon atoms;
m is an integer of 0 to 3, wherein
in a case in which m is no less than 2, a plurality of $R^C$s are identical or different from each other, a plurality of $R^D$s are identical or different from each other, and at least one of $R^A$, $R^B$, one or a plurality of $R^C$s and one or a plurality of $R^D$s represents a fluorine atom or a perfluoroalkyl group; and
* denotes a site that bonds to a sulfur atom of —S(=O)$_2$—O$^-$ in the formula (1).

10. The resist pattern-forming method according to claim 7, wherein $R^1$ in the formula (1) represents a hydroxy group, a hydroxyhydrocarbon group, a group comprising a lactone structure, an acyl group or a carbonyloxyhydrocarbon group.

11. The resist pattern-forming method according to claim 7, wherein the ring in $A^2$ in the formula (1) is an aromatic ring, an aliphatic ring, an aliphatic heterocyclic ring, an aromatic ring and an aliphatic ring, an aromatic ring and an aliphatic heterocyclic ring, or an aliphatic ring and an aliphatic heterocyclic ring.

12. A compound represented by formula (1):

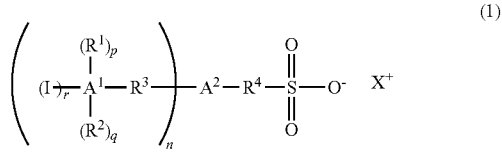

wherein, in the formula (1),
$A^1$ represents a group obtained from a compound which comprises a ring having 3 to 20 ring atoms by removing (p+q+r+1) hydrogen atoms on the ring;
$R^1$ represents a monovalent group having 0 to 10 carbon atoms which comprises at least one of an oxygen atom and a nitrogen atom;
$R^2$ represents a monovalent hydrocarbon group having 1 to 20 carbon atoms, a monovalent halogenated hydrocarbon group having 1 to 20 carbon atoms or a halogen atom;

p is an integer of 1 to 10, q is an integer of 0 to 9 and r is an integer of 1 to 10, wherein (p+q+r) is no greater than 11;

$R^3$ represents a single bond, —O— or —COO—;

$A^2$ represents an organic group having a valency of (n+1) and having 3 to 30 carbon atoms that comprises a ring having 3 to 20 ring atoms;

n is an integer of 1 to 3, wherein in a case in which there exist a plurality $R^1$s, the plurality $R^1$s are identical or different from each other, in a case in which there exist a plurality of $R^2$s, the plurality of $R^2$s are identical or different from each other, and in a case in which n is no less than 2, a plurality of $A^1$s are identical or different from each other, a plurality of $R^3$s are identical or different from each other, a plurality of p's are identical or different from each other, a plurality of q's are identical or different from each other, and a plurality of r's are identical or different from each other;

$R^4$ represents a fluorinated alkanediyl group having 1 to 10 carbon atoms; and $X^+$ represents a monovalent radiation-sensitive onium cation.

13. A method of generating an acid comprising irradiating the compound according to claim 12 with a far ultraviolet ray, an extreme ultraviolet ray or an electron beam.

\* \* \* \* \*